United States Patent [19]

Lopez et al.

[11] Patent Number: 5,690,612
[45] Date of Patent: Nov. 25, 1997

[54] MEDICAL CONNECTION INDICATOR

[75] Inventors: George A. Lopez, Corona del Mar, Calif.; Kathaleen K. Prince, Tampa, Fla.

[73] Assignee: ICU Medical, Inc., San Clemente, Calif.

[21] Appl. No.: 477,382

[22] Filed: Jun. 7, 1995

Related U.S. Application Data

[63] Continuation of Ser. No. 96,659, Jul. 23, 1993.

[51] Int. Cl.$^6$ ................................................. A61M 11/00
[52] U.S. Cl. ..................................... 604/93; 604/246
[58] Field of Search ................ 250/458.1, 462.1, 250/463.1, 465.1, 466.1; 604/93, 189, 246–247, 249, 251, 264, 280, 283, 411

[56] References Cited

U.S. PATENT DOCUMENTS

| | | | |
|---|---|---|---|
| 3,852,385 | 12/1974 | Huggins. | |
| 4,592,356 | 6/1986 | Gutierrez. | |
| 4,706,487 | 11/1987 | Bandou et al.. | |
| 4,832,214 | 5/1989 | Schrader et al.. | |
| 4,834,664 | 5/1989 | Lin. | |
| 4,878,897 | 11/1989 | Katzin | 604/86 |
| 4,928,212 | 5/1990 | Benavides. | |
| 4,943,896 | 7/1990 | Johnson. | |
| 4,969,883 | 11/1990 | Gilbert et al.. | |
| 5,009,490 | 4/1991 | Kouno et al.. | |
| 5,046,456 | 9/1991 | Heyman et al.. | |
| 5,256,155 | 10/1993 | Yerlikaya et al. | 604/246 |
| 5,401,245 | 3/1995 | Haining. | |
| 5,487,731 | 1/1996 | Denton | 604/100 |
| 5,556,388 | 9/1996 | Johlin, Jr. | 604/263 |

FOREIGN PATENT DOCUMENTS

| | | |
|---|---|---|
| 0 237 321 | 3/1987 | European Pat. Off.. |
| 0 399 119 | 11/1990 | European Pat. Off.. |
| 0 446 463 A1 | 12/1990 | European Pat. Off.. |
| WO 93/11828 | 6/1993 | WIPO. |

*Primary Examiner*—Corrine M. McDermott
*Attorney, Agent, or Firm*—Knobbe, Martens, Olson & Bear, LLP

[57] ABSTRACT

The invention relates to an indicator for use in indicating a medical implement that facilitates the passage of fluids either to or from a patient comprising a light emitting device affixed to said medical implement and related methods.

6 Claims, 25 Drawing Sheets

MEDICAL CONNECTION INDICATOR

RELATED APPLICATION

This application is a continuation of U.S. patent application Ser. No. 08/096,659, filed Jul. 23, 1993, pending, which is a continuation-in-part of PCT application Ser. No. PCT/US92/10367, filed Dec. 1, 1992, which designates the United States and claims priority from U.S. patent application Ser. No. 07/813,073, filed Dec. 18, 1991, which is abandoned. The disclosures of these related applications are incorporated herein in their entirety by this reference thereto.

BACKGROUND OF THE INVENTION

1. Field of the Invention

This invention relates to an indicator for use in indicating a medical implement that facilitates the passage of fluids either to or from a patient, which indicator comprises a light emitting device affixed to the medical implement, and related methods.

2. Background Discussion

The manipulation of fluids for parenteral administration in hospital and medical settings routinely involves the use of implements, such as connectors, adapters and valves, for facilitating the movement of fluids between two points. Most patients who require medical infusions of medication require infusions around the clock. Often, a patient requires medication every two or four hours. This situation forces healthcare workers to administer medication to patients during the day and at night. In order to properly administer medication to patients on a 24-hour basis, including during the hours when it is dark, the healthcare worker must either turn on the lights in the patient's room, often times waking up the patient, in order to locate the proper medical implement to administer medication to the patient, or carry a flashlight to locate the implement. Furthermore, in many cases, the manipulation of medical implements to administer medication requires two hands. Therefore, healthcare workers who administer medication are either forced to place the flashlight down on a piece of furniture or to hold it in their teeth.

This constant disturbing of the patient every two or four hours to administer medication results in the patient being unable to obtain a continuous period of restful sleep for more than two or four hours at a time. This lack of uninterrupted sleep results in a recognized psychological disorder referred to as Intensive Care Unit Psychosis. The effects of Intensive Care Unit Psychosis cause patients to become very irritable and, in some extreme cases, patients may act deranged by, for example, talking to themselves. Importantly, the ability of patients to recover from their ailments is endangered because of the deprivation of proper rest.

Some healthcare workers have tried to overcome these problems by carrying flashlights to avoid having to turn on the lights in the patient's room. However, many of the implements that are used to transfer medications to patients, such as, for example, fluid connectors for intravenous (IV) lines, require two hands for operation. Thus, there is no additional hand for the healthcare worker to hold the flashlight in order to illuminate the medical implement while making the necessary connection. Some healthcare workers have even resorted to holding the flashlight in their teeth to illuminate fluid connectors and the like while using both hands to administer the medication. However, holding a flashlight between one's teeth has resulted in such disfigurements as chipped teeth and other problems of hygiene associated with placing an unsanitary object in one's mouth. Other healthcare workers have tried to position the flashlight on a bed or nearby table and aim it at the implements to be manipulated. However, it is difficult to angle the flashlight to provide illumination at the right spot. Further, the flashlight often rolls off the bed or the table and onto the floor with a loud crash, ultimately waking up the patient and not solving the problem of disturbing patients while administering their medication. In addition, many hospitals cannot afford the cost of supplying each nurse with a flashlight nor the additional costs associated with loss or theft of the flashlights.

An indicator that will enable a healthcare worker to locate and manipulate medical implements, such as fluid connectors, for use in the administration of medications and other fluids, e.g., with IV lines, in a dark environment and that is which is easy to use would be of great benefit to the medical community.

SUMMARY OF THE INVENTION

The present invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its advantages, which include safety, reliable and repeatable performance, simplicity of manufacture and use, and the employment of an indicator that will clearly mark the position of a medical implement in a dark environment.

One aspect of the present invention relates to a medical fluid flow apparatus that provides an indication of its location in a dark environment. The medical fluid flow apparatus includes a medical implement (as defined hereinbelow) that facilitates the passage of fluids either to or from a patient, and also includes a light emitting device affixed to the medical implement. The light emitting device can take many shapes, such as an annular ring or a tapered annular ring. Further, the light emitting device can be of a variety of materials, including a plastic, such as polypropylene. In other embodiments, the light emitting device is a tape that emits light, a LED display, a light bulb or another light emitting material, such as a phosphorescent material. Zinc sulfide is one appropriate phosphorescent material for use as a phosphorescent material in connection with the present invention. If zinc sulfide is used, the zinc sulfide preferably constitutes about 25% to about 50% of the material of the light emitting device. In a particularly preferred embodiment, the zinc sulfide constitutes about 30% of the material of the light emitting device. The the light emitting device and the medical implement can be constructed as a unitary whole or the light emitting device can be affixed to the medical implement by any of a variety of ways. For example, the light emitting device can be affixed by way of one or more retaining ridges that are a part of the medical implement. Alternatively, the light emitting device can be affixed to the medical implement by way of locking ears that are a part of the medical implement. In one preferred form of the invention, the medical implement can be a valve having a fluid input receiving end and a fluid output discharging end. In this preferred form, the valve more preferably includes a body including a wall structure defining an internal cavity having a proximal end and a distal end, the proximal end having an opening sufficiently large to receive a delivery end of a medical implement which transfers fluid through the delivery end. The valve of this more preferred form also includes a spike having a tip, at least one hole located at or near the tip, and a passageway in communication with the hole that allows fluid to flow through the hole, the spike being seated inside the cavity such that the tip is enclosed within the cavity. This more preferred form of the valve as includes a resilient seal which is adapted to be moved into a compressed state upon insertion of the tip of the medical implement into the opening and an returns to an decompressed state upon removal of the tip. The seal in the decompressed state has a section which fills essentially completely a portion of the cavity adjacent the opening, with the seal section bearing against the wall structure near the opening to seal the opening, and in the compressed state the seal section being pushed by the delivery end of the medical implement away from the opening and into the cavity.

Another aspect of the present invention provides a method of administering a fluid to a patient in a dark environment with a medical implement that facilitates the passage of fluids to the patient. The method includes the following steps: (a) entering the dark environment, (b) locating the medical implement in the dark environment by locating an indicator affixed to the medical implement, where the indicator is a light emitting device affixed to the medical implement, (c) placing the medical implement in fluid communication with both the fluid and the patient, (d) administering the fluid through the medical implement to the patient in the dark environment, and (e) exiting the dark environment. The medical implement preferably has a first component and a second component, each of the components having an indicator that emits light in a dark environment affixed thereto. Where the preferred two-component medical implement is used, step (c) preferably includes attaching the first and second components together. In a particularly preferred form of this method, the first component is a medical valve, and the second component includes a delivery end through which may be administered a fluid from a source thereof to the patient, and the medical valve has an opening configured to receive the delivery end. Thus, step (c) can include the step of inserting the delivery end into the medical valve while in the dark environment.

Additional features and advantages of the present invention will be apparent to one having ordinary skill in the art upon reference to the ensuing detailed description.

BRIEF DESCRIPTION OF THE DRAWING

The preferred embodiments of this invention, illustrating all its features, will now be discussed in detail. These embodiments depict the novel and non-obvious methods and valves of this invention as well as the medical implement indicators and methods of use thereof, as shown in the accompanying drawing, which is for illustrative purposes only. This drawing includes the following Figures, with like numerals indicating like parts.

DETAILED DESCRIPTION OF THE PREFERRED EMBODIMENTS

The preferred embodiment of the indicator of the present invention is designed for use with a wide variety of medical implements as defined below. The medical implement indicator of the present invention is a light emitting device, such as, for example, a glow ring, that is affixed to the medical implement and that allows a healthcare worker to find and keep track of a medical implement in the dark. A detailed description of several embodiments of the present invention is provided below The term "proximal" is used to denote the end of the valve and other components at or near the spike tip 32 in FIGS. 2 through 5, 10 through 12, 14, 16, 23 and 24 and at or near the spike tip 60 in FIG. 6, and at or near the seal cap 92 in FIGS. 8, 9, and 13 through 19. The term "distal" is used to denote the opposite end of the valve, or spike tip, or seal. The term "medical implement" is used to denote any medical tool known to those of skill in the art that can facilitate the passage of fluids, particularly liquids, therethrough. Examples of medical implements that are contemplated include, but are not limited to, tubing, conduit, syringes, IV sets (both peripheral and central lines), piggyback lines, medical valves, and other components. Medical implements are commercially available in standard sizes. Thus, either or both ends of the valve can be provided with fittings to accommodate such standard size medical implements.

Figures 1, 2:
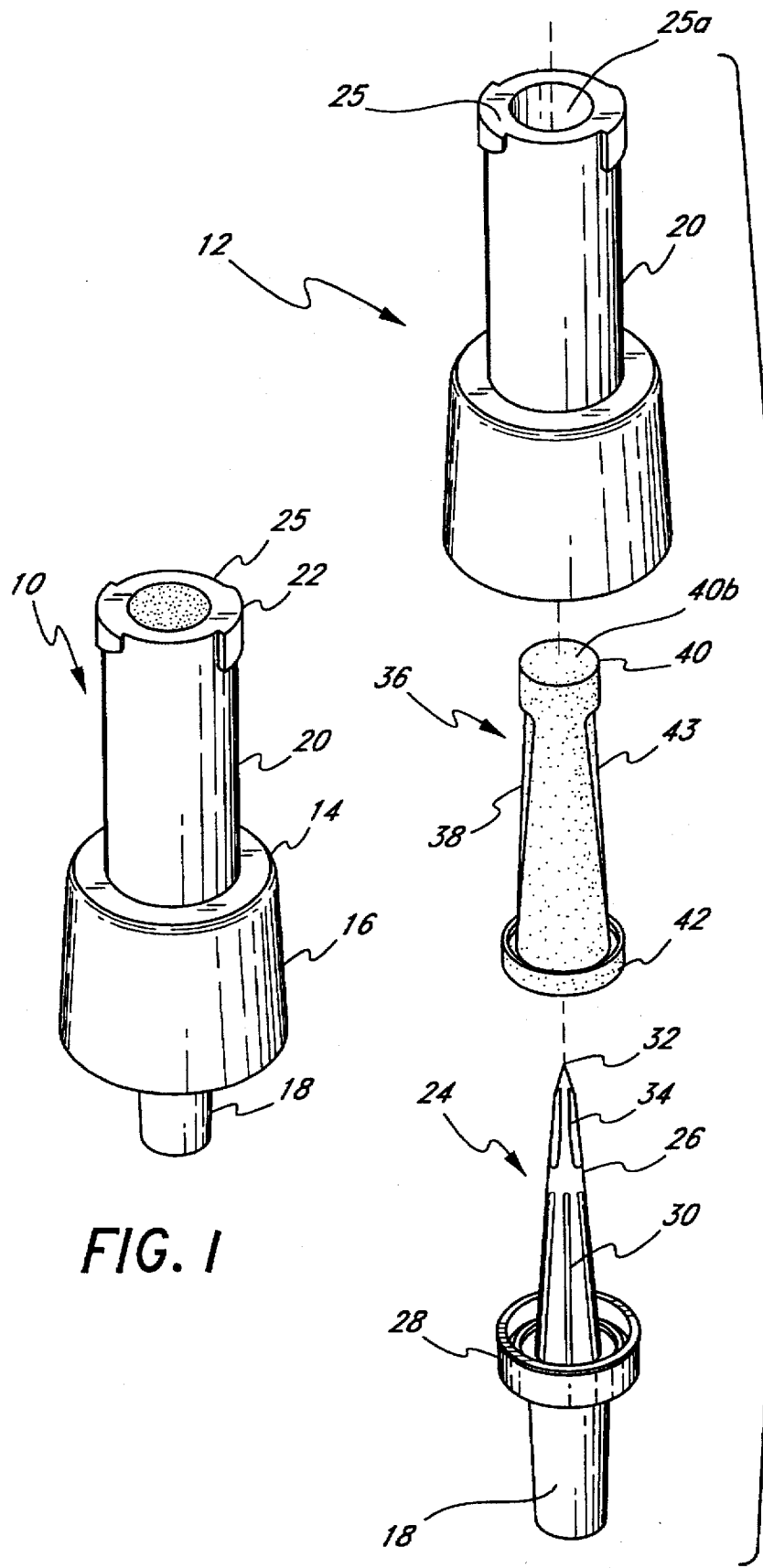
FIG. 1 is a perspective view of the first embodiment of a valve useful in connection with this invention.
FIG. 2 is an exploded perspective view of the valve shown in FIG. 1 illustrating spike, seal, and body or housing components of the invention.
Figure 3:
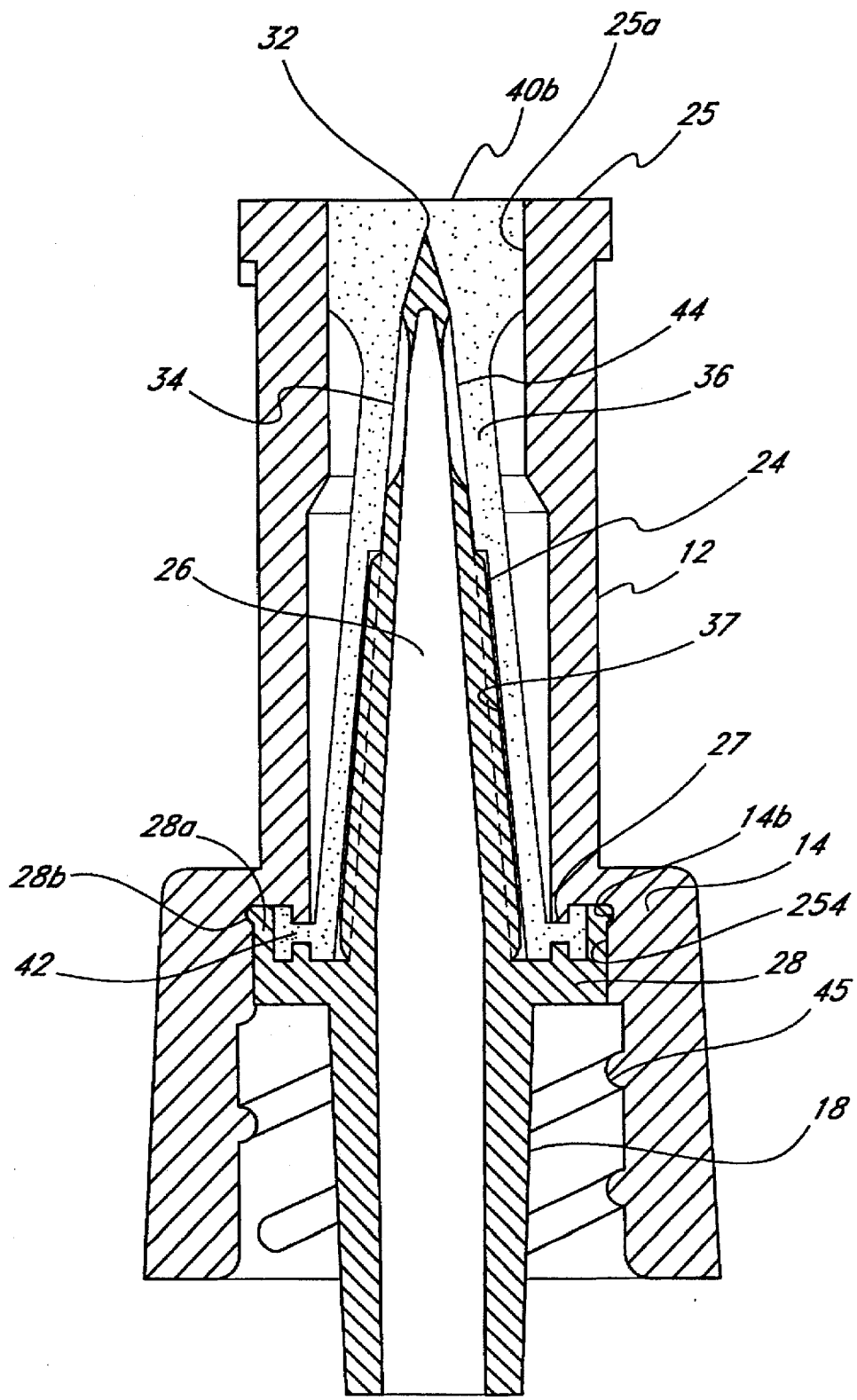
FIG. 3 is a longitudinal cross-sectional view of the assembled valve of FIG. 1.
Figure 4:
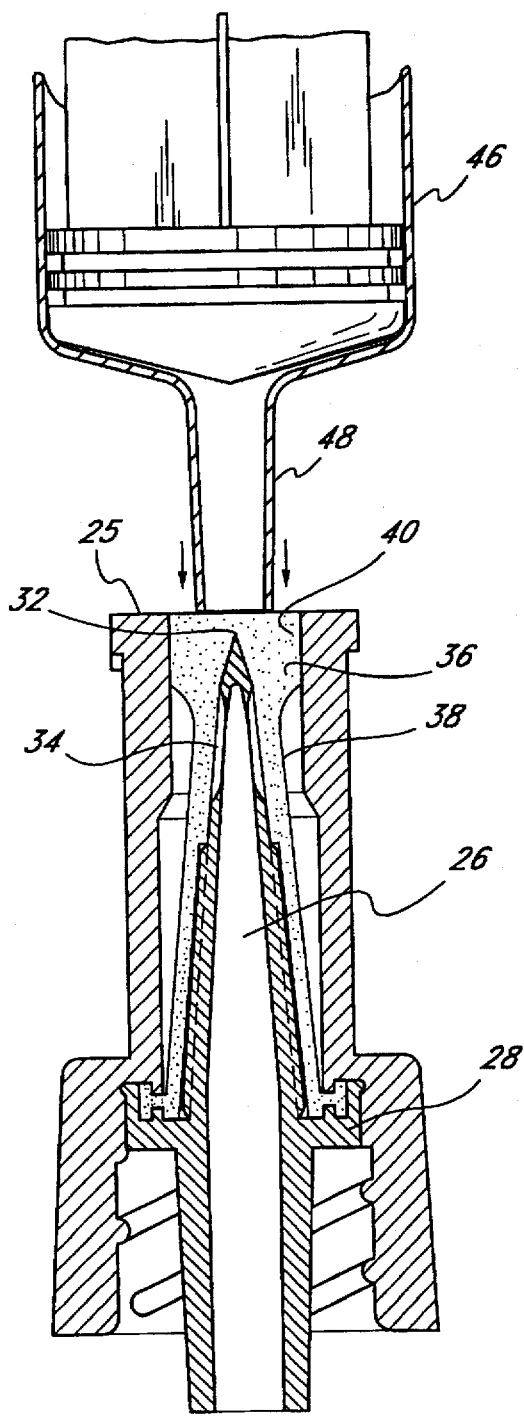
FIG. 4 is a schematic, longitudinal, cross-sectional view of the assembled valve of FIG. 1 before compressing the seal.
Figure 5:
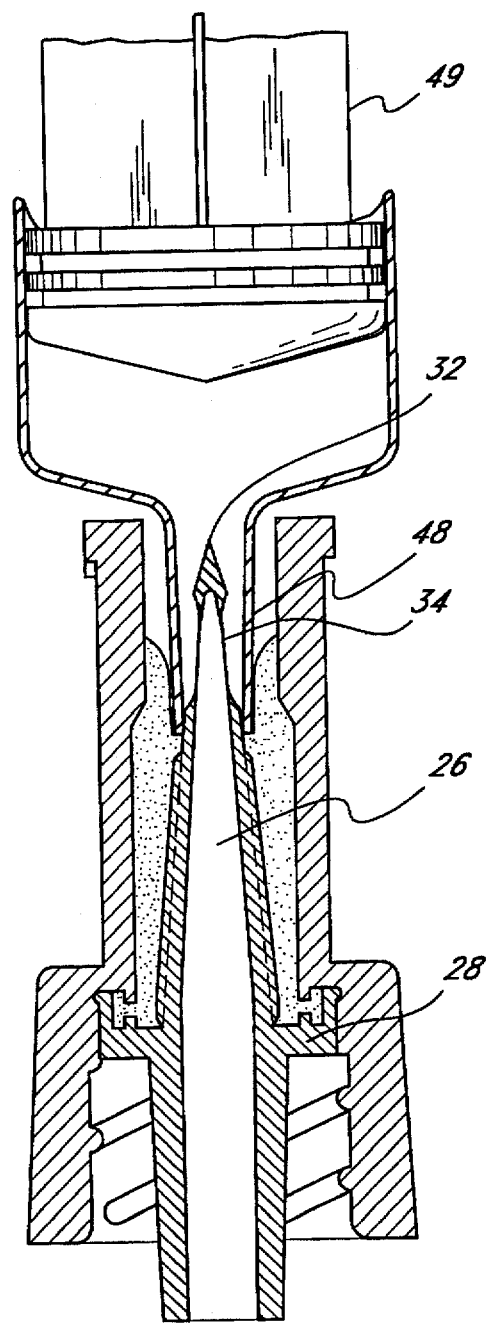
FIG. 5 is a schematic, longitudinal, cross-sectional view similar to FIG. 4 showing the valve during compression of the seal.
Figure 13:
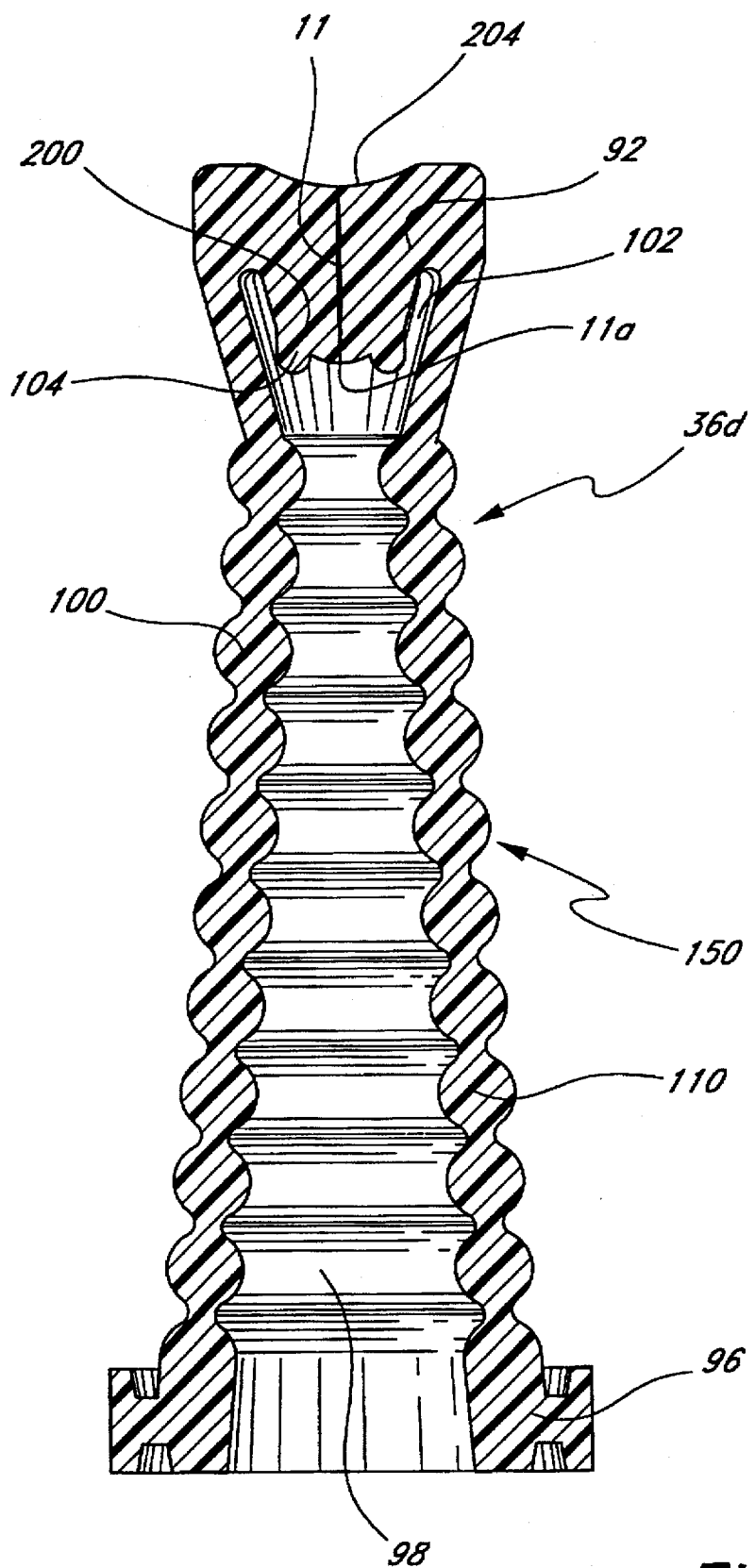
FIG. 13 is a longitudinal cross-sectional view of an additional embodiment of the seal.

As best shown in FIGS. 1 and 2, the first embodiment of valve 10, includes a valve body or housing 12, a spike element 24, and a seal 36. The seal 36 is prepared from a resilient material that is flexible, inert, impermeable to fluid, and readily pierceable by the spike 26. In the valve embodiment shown in FIG. 13 depicting an alternate shaped seal 36d, this seal 36d has a precut slit 11 in its proximal end. This provides a tiny orifice through which the tip 32 of the spike element 24 may easily pass, yet still provides a fluid tight seal upon withdrawal of the spike element. These three components are assembled, as depicted in FIG. 3, with the spike element 24 enclosed to prevent accidental sticks. FIG. 2 illustrates how the housing 12, seal 36, and spike element 24 are attached without the need to use any adhesive or other bonding agent or process. Mechanical connection which provides a fluid tight closure is attained as is discussed subsequently. As shown in FIGS. 4 and 5, the seal 36 moves within the housing 12, being pierced by the spike element 24 to expose the tip 32 of the spike element 24 to allow fluid to flow through the valve 10.

Referring to FIG. 1, one preferred embodiment of the housing 12 has a bell-shaped skirt 16 and an upper, preferably cylindrical, conduit 20. The skirt 16 is integral with, and connected by an annular ring 14, to the upper conduit 20. The skirt 16 creates a shield for an inner conduit 18 of the spike element 24. This inner conduit 18 is preferably cylindrical in shape, and slightly tapered. Inner conduit 18 and upper conduit 20 comprise aligned hollow tubes so that inner conduit 18 and upper conduit 20 are in fluid communication with one another when the spike element 24 pierces the seal 36. There is an annular lip 25 surrounding a circular opening 25a in the top of the conduit 20 (see FIG. 2).

In the first embodiment of the valve, the upper conduit 20 is adapted to receive the tip or nose 48 of an ANSI standard syringe 46 (see FIGS. 4 and 5). It is, however, contemplated that the outer diameter of the upper conduit 20 can be of any size to accommodate the attachment of other connector devices thereto. Advantageously, the proximal end of the upper conduit 20 can be equipped with a locking mechanism to facilitate locking of the valve 10 to a variety of medical implements. For example, referring to FIG. 1, locking ears 22 near the proximal lip 25 of housing 12 are preferably provided such that the housing 12 can be locked into any compatible Luer-Lock device known to those with skill in the art. For example, referring to FIG. 19, conventional Luer-Lock threads 180 can be provided on the outer diameter of upper conduit 20.

Referring to FIG. 2, the spike element 24 has at its distal end the inner conduit 18 and at its proximal end a hollow spike 26 which is integral with the inner conduit. The inner conduit 18 and spike 26 present a continuous passageway for fluid during use. An annular cuff 28 on an intermediate portion of the spike element 24 is integral with, and interconnects, the inner conduit 18 and the spike 26. As illustrated in FIG. 3, the rim 28a of the cuff 28 abuts the underside of the inner ring 14, and has an annular detent 28b that snaps into an annular groove 14b in the underside of the ring. The cuff 28 serves two functions. First, it serves as an attachment device to the underside of the annular ring 14. Second, it serves as a support and attachment device for the seal 36.

The hollow spike 26 has a tapered conical shape, ending in a sharp, pointed tip 32. Preferably, along the length of the spike are raised, protruding ridges 30. These raised ridges 30 extend from the surface of the spike preferably between 0.2–2.0 mm. The ridges 30 are preferably aligned along the length of the spike as illustrated in FIG. 2. These ridges 30 serve to break any vacuum created when the spike 26 is sealed as described hereinbelow. Modifications to the alignment and orientation of the ridges are discussed hereinbelow in association with their function. Just distal the spike tip 32, there is situated at least one longitudinal through-hole 34 to permit fluid communication between the inner conduit 18 and the upper conduit 20. Preferably, there are three through-holes 34 within about 0.200 inch from the spike tip 32. These through-holes 34 may be of any size, however, the larger the size of the through-holes the greater the fluid flow rate through the valve 10. In a preferred valve embodiment, the size of the through-holes 34 are 18-gauge to provide a flow rate three times that of a standard 18-gauge needle.

The seal 36 has a seal cap 40 with generally flat top surface 40b, an outwardly tapered sidewall 38, and a lower lip 42. Its interior is hollow to provide the conically shaped cavity 37 (FIG. 3). Thus, the seal 36 slips easily over the spike element 24 to fit snugly within the cavity 37. The seal lip 42 is seated within the annular cuff 28 and wedged between the cuff and the underside of the ring 14. There are longitudinal grooves 43 (FIG. 2) along the length of the seal 36 which provide air pockets that facilitate compression of the seal 36 during use. The grooves 43 may be of variable shape or size to facilitate seal compression. In the first valve embodiment, there is a single groove 43 which completely surrounds the seal 36 between the seal cap 40 and the lip 42.

The base of the seal 36 has a width such that the seal lip 42 fits snugly into the annular cuff 28. The hollow interior or cavity 37 (FIG. 3) of the seal 36 is preferably tapered to conform internally to the shape of the spike 24, having a wall portion 44 which contacts the spike 24 distal seal cap 40. The exterior of the seal 36 is sized and shaped to fit inside the upper conduit 20 of the housing 12. The cap 40 reseals the valve 10 when the top surface 40b is above the through-holes 34. Preferably, the cap 40 substantially fills the opening 25a in the top of the conduit 20. Thus, after assembly, the top surface 40b of the seal cap 40 is essentially flush with the lip 25, so that the lip 25 and seal cap 40 can be swabbed with alcohol or other disinfectant without leakage of disinfectant into the valve 10. It is important that the surface 40b be exposed so that it may be swabbed with a disinfectant.

As best shown in FIG. 3, the spike 24, with contiguous inner conduit 18, is affixed to the housing 12 through the association of the external potion of annular cuff 28 and the internal portion of annular ring 14. Although not necessarily required, these two pieces may be affixed by any one of a variety of methods known to those of skill in the art including, but not limited to, heat sealing, glue, pressure lock, bonding or the like. The seal 36 fits into the annular cuff 28 and is held in place by an internal lip 27 along the internal portion of the annular ring 14 of the housing 12. The length of the spike 24 is such that, after assembly, the tip of the spike rests below the plane defined by the lip 25 of the housing 12. Preferably, the spike tip 32 is approximately from 0.525" to 0.1" below the lip 25 of the housing 12. The seal 36 fits snugly against the spike 24 and is essentially flush with the lip 25 of the housing 12. The spike tip 32 is thus embedded within the seal cap 40 prior to use or may be approximately 0.025" distal the seal cap 40 when the valve 10 is in the closed position. The inner conduit 18 is partially shielded by the bell shaped skirt 16 of the housing 12 (see FIGS. 1–3). The inner surface of the bell shaped skirt 16 preferably has protruding threads 44 as an optional locking mechanism for attaching a medical implement thereto. Further, other medical devices can be pressure fit over the outer portion of inner conduit 18 without direct association with the protruding threads 44.

During use, the valve is designed to be adapted as a two-way valve. The orientation of the valve is independent to fluid flow and dependent on the preferred orientation of the preexisting connections. Thus, the valve can be used as a valve connector for an intravenous central or peripheral piggyback connector in either orientation. Parenteral fluid is delivered to patients through tubing such that the liquid flows from a container through a piercing element into the patient. The containers are frequently changed or additional fluid bottles are added. The valve disclosed herein is designed to interconnect medical implements along the route of fluid delivery to the patient. However, the valve is also useful in any environment in which a resealable fluid valve is desired. During use, a connector of the appropriate size is fitted over the inner conduit 18. Locking can be achieved by a Luer-Lock mechanism, a pressure fit or any other locking mechanisms known to those with skill in the art, as described above. Thus, in one example, fluid passes from the inner conduit 18 into the spike 26. However, fluid flow is locked in place by the seal 36.

FIGS. 4 and 5 illustrate valve activation. In FIG. 4, the medical implement connecting to the proximal end of the valve 10 is a syringe 46. However, this connecting implement could be any number of medical implements known to those of skill in the art. The nose 48 of the syringe 46 is placed on the seal cap 40 inside the lip 25 of the housing 12. The application of pressure on the syringe 46 in the direction of the arrows, as illustrated in FIG. 4 creates pressure on seal cap 40. The resulting downward pressure compresses the seal 36. This pushes the tip 32 of the spike 26 through the seal cap 40 to expose the through-holes 34. Compression is facilitated by the grooves 38. Fluid is now able to flow into the syringe 46, or vice versa, depending on whether fluid is to be withdrawn from the patient or medication injected into the patient. FIG. 5 shows valve 10 opened by insertion of the nose 48 of the syringe 46 into the opening 25a. A syringe plunger 49 in the syringe 46 is retracted thereby creating a vacuum to draw fluid through the valve 10 into the syringe. For intravenous applications, the valve 10 can be orientated in the position diagramed in FIGS. 4 and 5, or it can be rotated 180° such that fluid flows in the opposite direction.

Upon removal of the syringe from the spike 26, as shown in FIG. 4, the seal 36 is free to return to its original shape and cover the through-holes 34. The ability of the seal 36 to return to its original shape is determined by the resiliency of the material used to prepare the seal 36. In addition, the ability of the seal 36 to return to its original shape is facilitated by the protruding ridges 30 formed on the external surface of the spike. During compression, a vacuum may form in the area between the spike 26 and the seal 36, thereby preventing the seal 36 from returning to its original position. The protruding ridges 30 permit air to pass along the spike/seal interface to prevent vacuum formation and allow free return of the seal 36. The ability of the seal 36 to deform reversibly and return to its original position is particularly useful because (1) it immediately stops fluid flow through the valve 10, (2) it covers the recessed spike 26 to maintain its sterility, and (3) it reduces the risk that the spike could inadvertently pierce another object or person. In addition, since the valve 10 lacks movable parts, except for the seal, it is unlikely that when the seal 36 is pushed down, the valve 10 would fail to function.

Advantageously, the through-holes 34 are located relatively low on the spike 26. Thus, the through-holes 34 are sealed relatively early in the process as the seal 36 returns to its original configuration when the valve 10 is closed. In one preferred embodiment of the valve, the through-holes 34 are located 0.075" below the spike tip 32 (see FIG. 2). Additionally, the through-holes 34 are sealed even if the seal 36 does not fully return to its original configuration depicted in FIG. 4. Further, the ability of the seal 36 to return reversibly to its original position permits the reuse of the valve 10. Following disconnection, and before reuse, the surface of pierced seal cap 40 is essentially flush with the housing 12. Thus, this flush surface can, advantageously be sterilized with alcohol or other surface decontaminating substances. The skirt 16 and upper conduit 20 advantageously shield both connections from the surrounding environment to protect the sterility of the connection. Further, both the skirt 16 and upper conduit 20 function as collection reservoirs to prevent fluid from dripping from the valve 10 during manipulation.

A cover cap (not shown) can be supplied to fit over the upper conduit 20 as further protection for the seal surface between use. Such a cover cap, however, is not needed to maintain sterility since the seal 36 may be swabbed with a disinfectant after each use. The reversibility of the seal 36 makes the valve 10 particularly attractive as a connector valve to provide fluid communication between two fluid lines. Therefore, the valve provides for placing a first fluid line in communication with a second fluid line using the valve disclosed herein. The reversibility of the valve 10 permits multiple fluid lines to be successively added, for example, to a fluid line in direct communication with a patient's vein. Since the valve is easily sterilizable and sealable, fluid lines can be added and removed without disconnecting venous contact.

The valve 10 is preferably prepared from a hard plastic, such as ABS plastic, but it is additionally contemplated that the valve could be prepared from other medically inert materials known to those in the art. The spike element 24 is preferably prepared from the same material as the housing 12. However, a stronger material, such as a poly-carbonate material, may be desirous for the spike element 24 to enable it to pierce a variety of connecting septums and seals. One particular advantage of this valve is that it does not rely on the use of metal needles. This dramatically reduces the risk of skin puncture during use and manufacture. Further, the upper conduit 20 serves as a shield to the spike 26 such that skin puncture is further reduced. The spike 26 need only be strong enough to penetrate the seal cap 40, or if necessary, to pierce a connecting septum.

In the embodiment of the valve illustrated in FIGS. 2–4, the through-holes 34 are placed distal spike tip 32. This placement provides two important advantages. First, the placement of the through-holes 34 facilitates resealing of the valve 10 after use. Second, if the through-holes were placed at the spike tip 32, the holes 34 may core the seal cap 40 thereby introducing seal particulate into the fluid flow and possibly plug the holes 34. Thus, the longitudinal placement of the through-holes distal the spike tip 32 prevents the introduction of particulates into the fluid path and/or plugging of the through-holes 34. It is additionally contemplated that the number and diameter of the through-holes 34 can be adjusted to accommodate different fluid velocities. In a preferred embodiment of the valve, the preferred velocity of fluid passing through the through-holes 34 is equal to or greater than the flow rate through an 18-gauge needle. Through-holes larger than 18 gauge will, of course, facilitate greater fluid flow rates.

An important advantage of the valve 10 is that it has very little dead space, thus the volume of liquid entering into the valve 10 is substantially equivalent to the volume of fluid leaving the valve 10. Further, the total equivalent fluid volume of the valve is very small such that the volume of fluid flowing through the system in order to place the valve 10 in fluid communication with a medical implement such as a syringe 46 is substantially zero.

Figure 6:
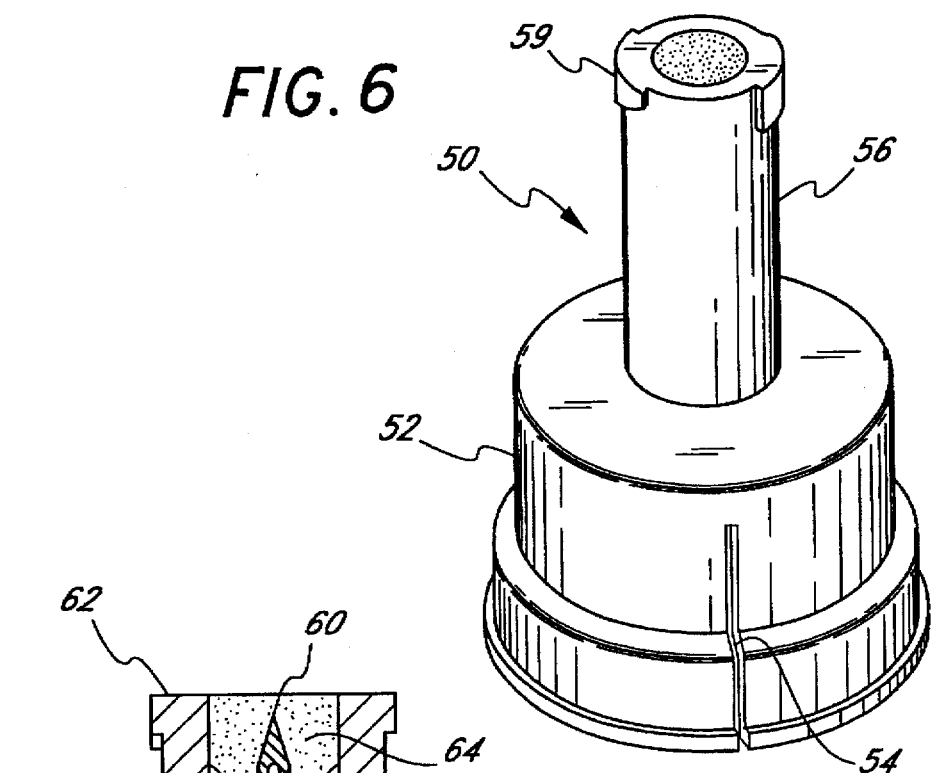
FIG. 6 is a perspective view of a second embodiment of a valve useful in connection with the present invention.
Figure 7:
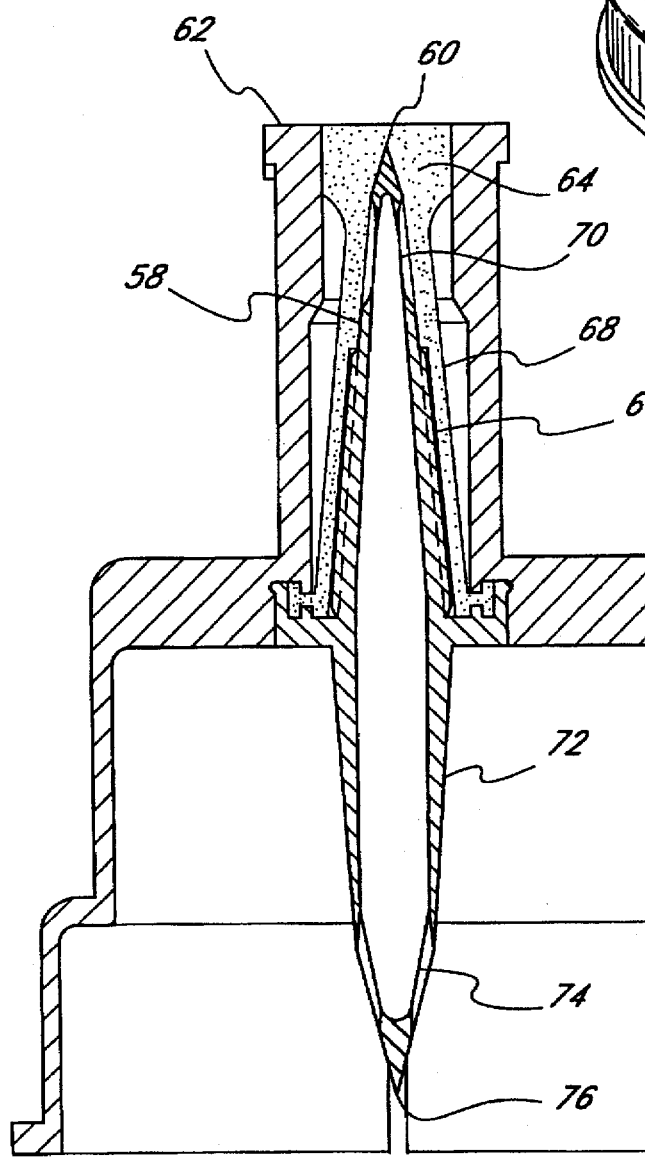
FIG. 7 is a longitudinal cross-sectional view of the valve of FIG. 6.

In another preferred embodiment of the valve, illustrated by FIGS. 6 and 7, a disposable sterile adaptor valve 50 is provided to function as a resealable lid for a container (not shown) of fluid. The fluid can thus be removed from the fluid container or permitted to flow from the container into a medical implement adapted to house fluid in a sterile manner. As is the conventional practice, an open mouth of the container will ordinarily be sealed with a cover member (not shown).

FIG. 6 shows an adaptor valve 50 having a body including an adaptor skirt 52. The adaptor skirt 52 will preferably fit snugly over the open mouth of the container. The skirt 52 may be of any size to accommodate a range of container sizes. A lengthwise slit 54 is preferably provided in at least one location along the length of the skirt to ensure a snug fit between the skirt 52 and the container. A chamber 56, preferably tubular in configuration, extends upward from the skirt 52 and is similar in construction and design to the upper conduit 20 of the first preferred valve embodiment. Similar to the first valve embodiment, the proximal portion of the valve may contain a locking mechanism 59 that preferably comprises a Luer-Lock device or other locking device known to those of skill in the art.

As depicted in FIG. 7, a spike 58 extends upward through a tubular chamber 56. A spike tip 60 is preferably recessed from a proximal lip 62 of the tubular chamber 56. In a closed position, this tip 60 is covered by a seal 64, which is essentially the same as seal 36. Protruding ridges 66 and seal grooves 68 facilitate seal compression and promote closure following use. Thus, in the closed position as illustrated in FIG. 7, the seal 64 covers the through-holes 70 to prevent fluid out-flow from the container. The adaptor valve 50 contains a second spike 72 which points in the opposite direction as the spike 58. These spikes 52 and 72 are in fluid communication with each other. The spike 72 extends downward inside the adapter skirt 52. The two spikes preferably form one component of the valve 50 while the skirt 52 and upper chamber form a second component. These two components can be assembled in a manner like that of the valve 10. The spike 72, like the spike 58, has longitudinal through-holes 74 and a tip 76. The through-holes 74 are located inward of the tip 76. The adaptor valve 50 is thus useable with containers holding sterile medicament having a cover or septum seat at the open mouth of the container. Examples of containers with such seals contemplated for use with this valve include dosage bottles for intramuscular injector antibiotic containers or the like. However, it is also contemplated that the valve 50 can be adapted with its own seal and locking mechanism to permit the valve to be employed on a variety of containers for medicaments or other fluids. Medicaments in these types of containers are preferably maintained under sterile conditions and the volume and nature of the medicament is such that multiple aliquots are intermittently removed over time. If the medicament is reconstituted, then, during use, any covering over the opening on the container is removed to reveal the rubber septum. The adaptor valve 50 is placed over the septum and direct pressure is applied to pierce distal spike 72 through the septum and into the container. A syringe or the like can then be applied, as depicted in FIG. 4, in association with the first preferred valve embodiment, to withdraw fluid from the container. The pressure of the nose 48 over the spike 58 pushes the spike tip 60 through the seal 64. At the same time, the seal 64 is compressed. Compression is accommodated by the seal grooves 68. Fluid is withdrawn from the container and the syringe is removed from the spike 58. Release of the pressure applied to the seal 64 permits the seal 64 to return to its original configuration. The spike ridges 66 facilitate movement of the seal 64.

Often the ingredients housed in containers are those that can be lyophilized at purchase. Lyophilized ingredients require reconstitution before use. If the medicament requires reconstitution before use, then sterile water, saline, or other fluid can be introduced into the container before fluid is extracted. The two-way nature of the valve permits this without any special adaptation. After the syringe is removed, the adaptor valve 50 automatically seals. Subsequently, aliquots can be removed from the container by syringe or the like. Alcohol or other compatible surface sterilizing agents can be used to wipe the lip 62 and seal 64 before each use. Similar to the first valve embodiment, it is additionally contemplated that a cap can be provided to fit over the upper chamber lip 62 between uses.

The adaptor valve 50 can be adapted to function as a medicament adaptor for an intravenous container. In this case, the adaptor valve 50 is placed on a medicament container for intravenous delivery and attached via tubing to an intravenous feed. Thus, the adaptor valve 50 can be placed in fluid communication with a connector valve of FIG. 1 to facilitate the flow of medicament from intravenous drip bottles.

Figure 9:
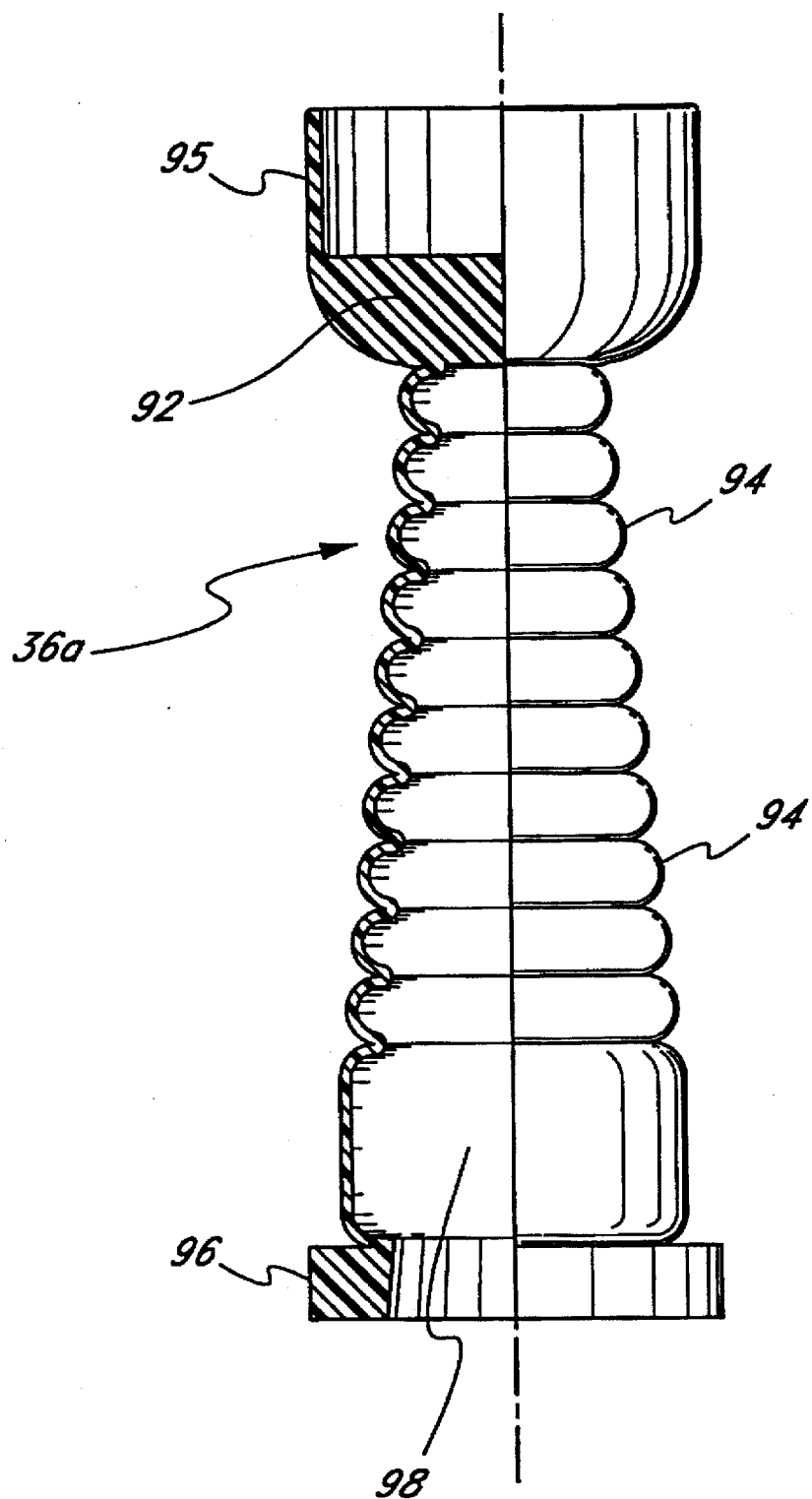
FIG. 9 is a side elevation view, partially in cross-section, of an embodiment of the seal.

An alternative embodiment of the seal, a seal 36a, is shown in FIG. 9. The seal 36a comprises a seal cap 92 at the proximal end thereof and a seal lip 96 at the distal end thereof. A cup-like annular flange 95 is provided proximal the seal cap 92. The seal cap 92 and seal lip 96 are connected by a seal wall consisting of a plurality of ringed wall portions 94 that expand and collapse in an accordion like fashion. During compression of the seal 36a, the diameter of the ringed wall portions 94 expand outward in the radial direction. There are air pockets 13a (FIG. 10) between ring portions 94 and the housing and air pockets 13b between the spike 24 and seal 36a. The seal 36a contains a cavity 98 distal the seal cap 92 and adjacent the ringed wall portions 94. The seal 36a interacts with the spike 26 (FIG. 2) and other components of the valve in a similar fashion to the seal 36 of FIG. 2.

Figure 10:
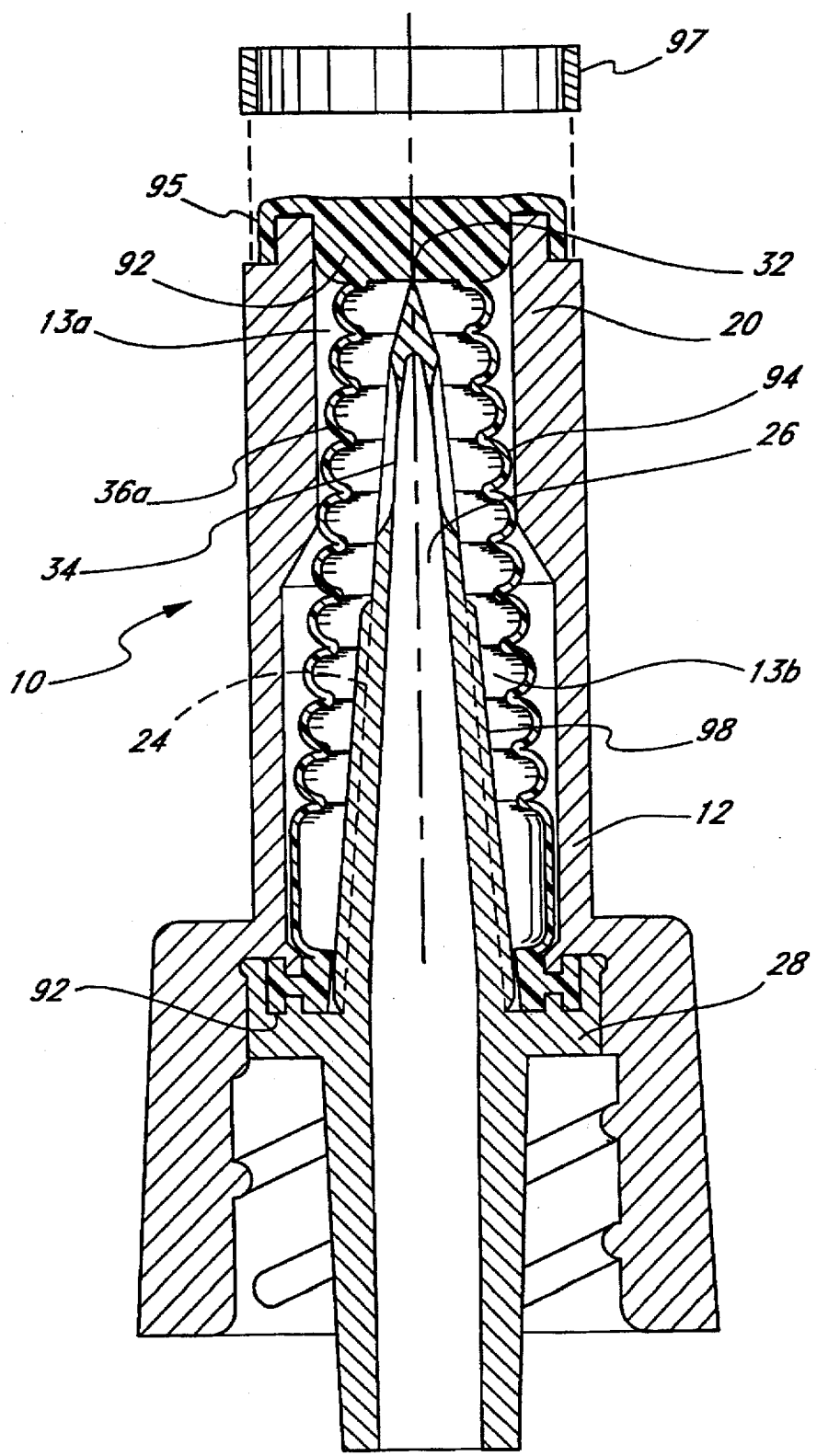
FIG. 10 is a longitudinal cross-sectional view of the assembled valve of FIG. 1 using the seal of FIG. 9.

Referring to FIG. 10, the cup-like annular flange 95 can be stretched around the upper conduit 20 and held in place by an annular ring 97. This creates a trampoline-like effect that assists returning the seal 36a to a decompressed state after withdrawal of a syringe (not shown). This embodiment has two advantages. First, the proximal end of the valve 10 can be swabbed with alcohol or other disinfectant without leakage of disinfectant into the valve 10. Second, by affixing the cup-like annular flange 95 to the upper conduit 20 at the proximal end thereof with the annular ring 97, the repeated deformation and reformation of the seal 36a is assisted.

Figure 11:
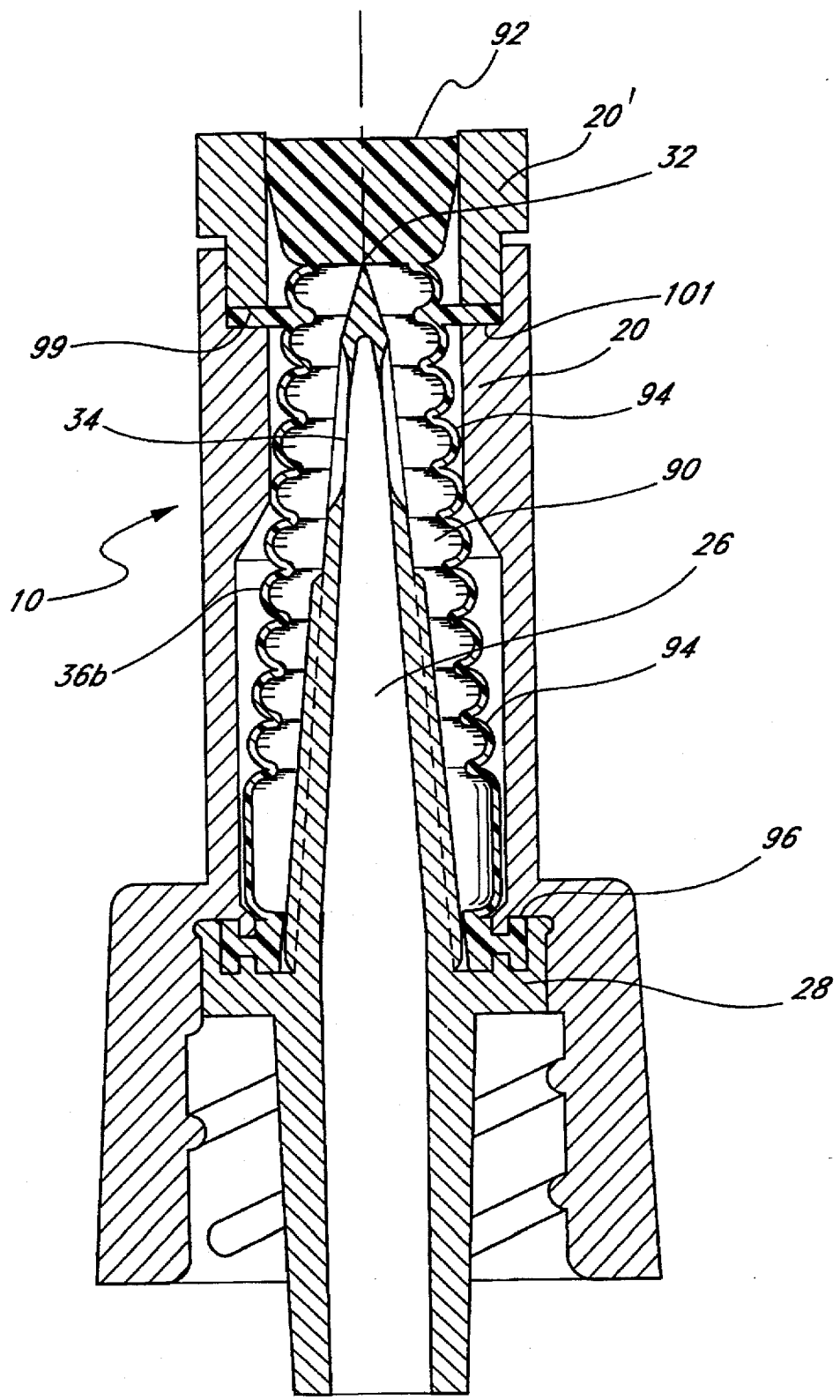
FIG. 11 is a longitudinal cross-sectional view of the assembled valve of FIG. 1 using another embodiment of the seal.

In an alternative embodiment of the seal, the seal 36b is shown in connection with the valve 10 in FIG. 11. The seal 36b is similar to the seal 36a shown in FIGS. 9 and 10, as the seal 36a is comprised of a seal cap 92, a side wall consisting of ringed wall portions 94 and a seal lip 96. The seal 36a also has an outwardly extending ring 99 which is at a right angle with respect to the longitudinal axis of the valve 10. This ring 99 is used to attach the seal 36b to the upper conduit 20. Preferably, an upper conduit annular plug 20' is inserted within the upper conduit 20 to create a tight fit between the perpendicular ring 99, a ledge 101 in the upper conduit 20, and the plug 20'. The ring 99 assists in the reformation of the seal 36b to enclose the spike 26 upon withdrawal of a syringe (not shown).

Figure 12:
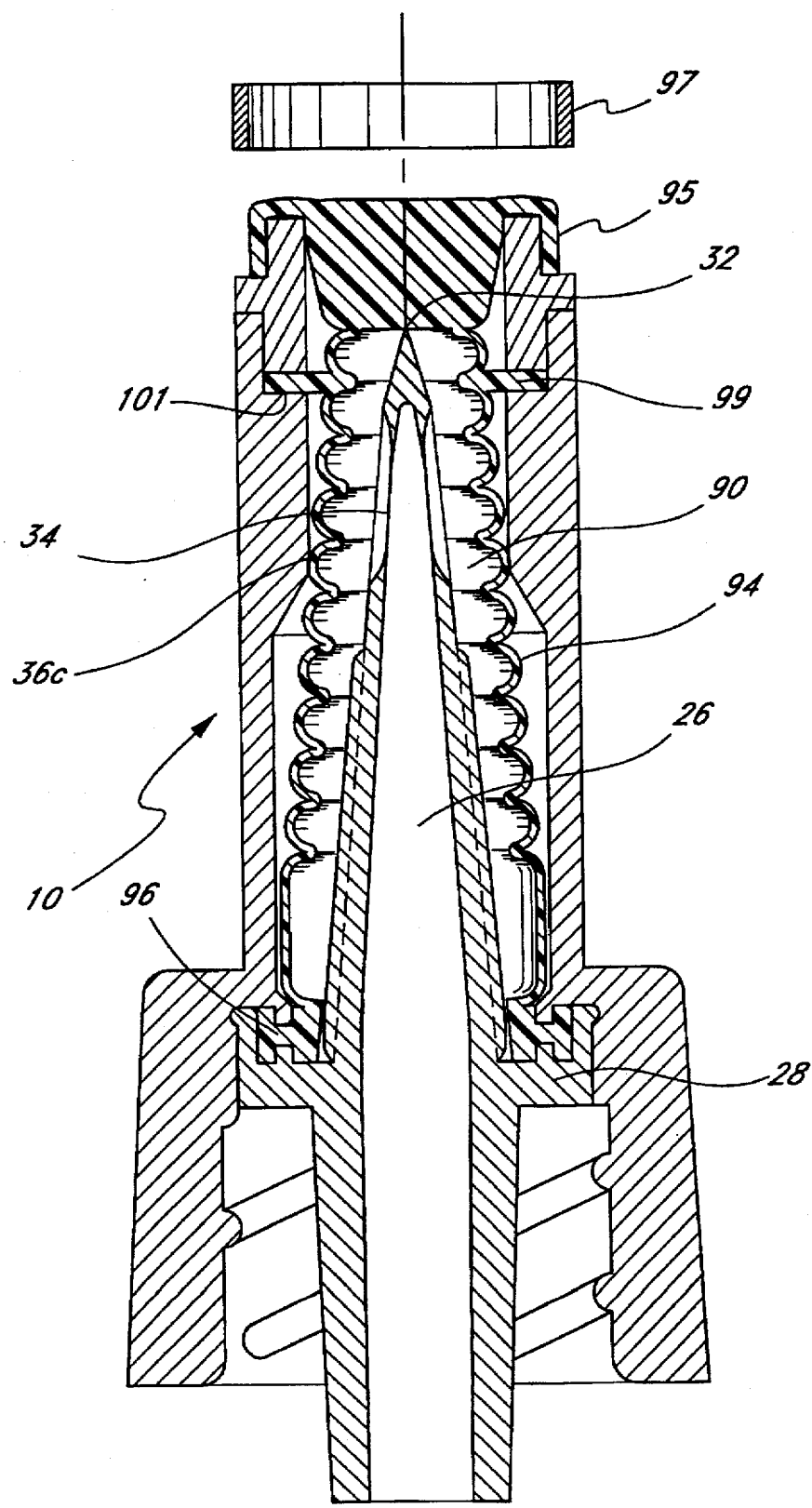
FIG. 12 is a longitudinal cross-sectional view of the assembled valve of FIG. 1 using yet another embodiment of the seal.

As shown in FIG. 12, the cup-like annular flange 95 and ring 99 may both be used in connection with the valve 10, to provide the seal 36c. This seal 36c, provides rapid reformation upon withdrawal of a syringe (not shown) and realizes the advantages of both the seals 36a and 36b.

Another alternative embodiment of the seal, a seal 36d, is shown in FIG. 13. In this embodiment, the seal 36d is comprised of a seal cap 92, a seal lip 96, and a side wall 150 comprised of circular tires 100 stacked in series one on top of an adjacent larger diameter lower tire. The circular tires 100 are preferably solid throughout the diameter of the cross-section thereof. These circular tires 100 will deform and reform upon, respectively, compression and decompression of the seal 36d, thereby exposing or covering a spike (not shown) as the case may be.

Figure 14:
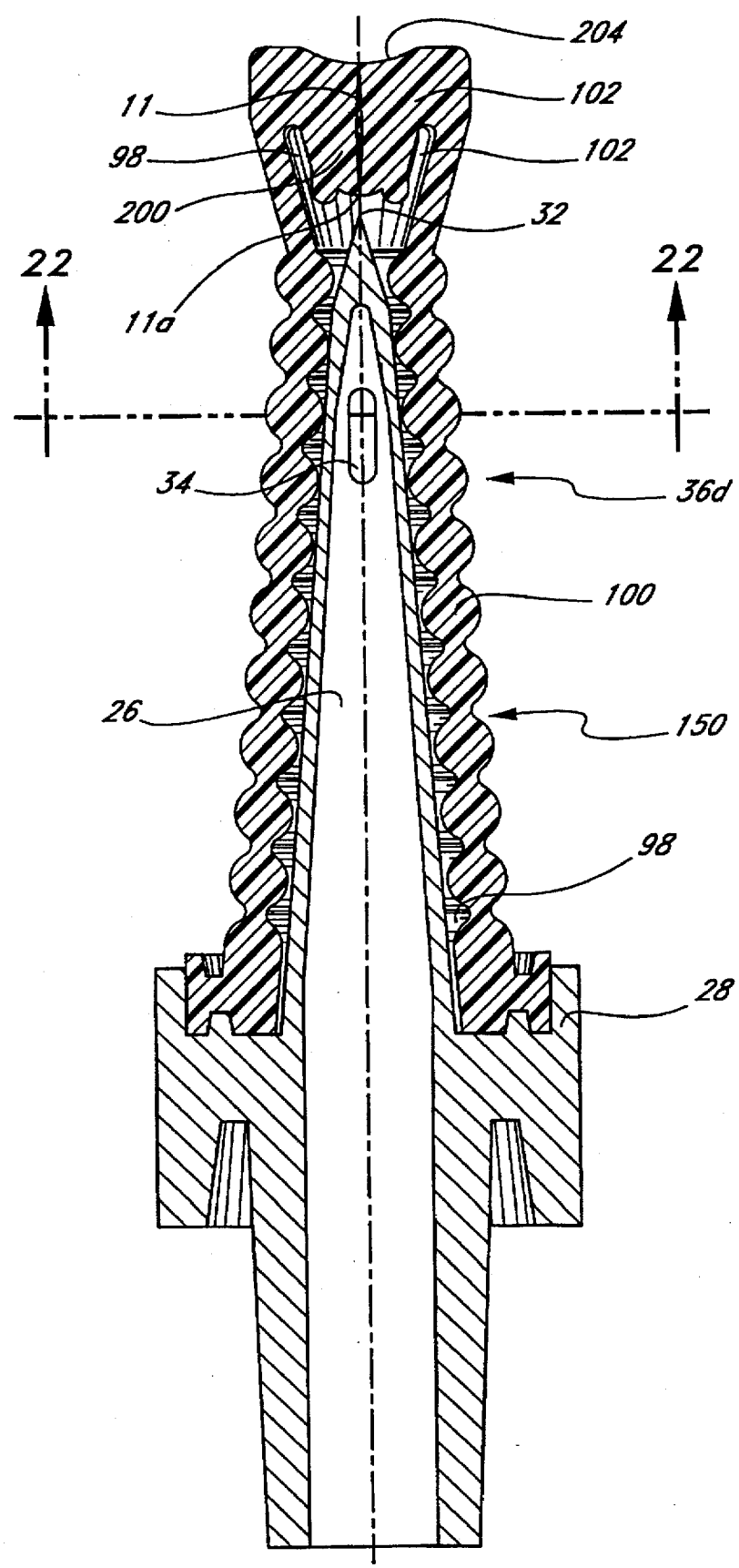
FIG. 14 is a longitudinal section of the seal shown in FIG. 13 used in connection with the spike device shown in FIG. 2.
Figure 15:
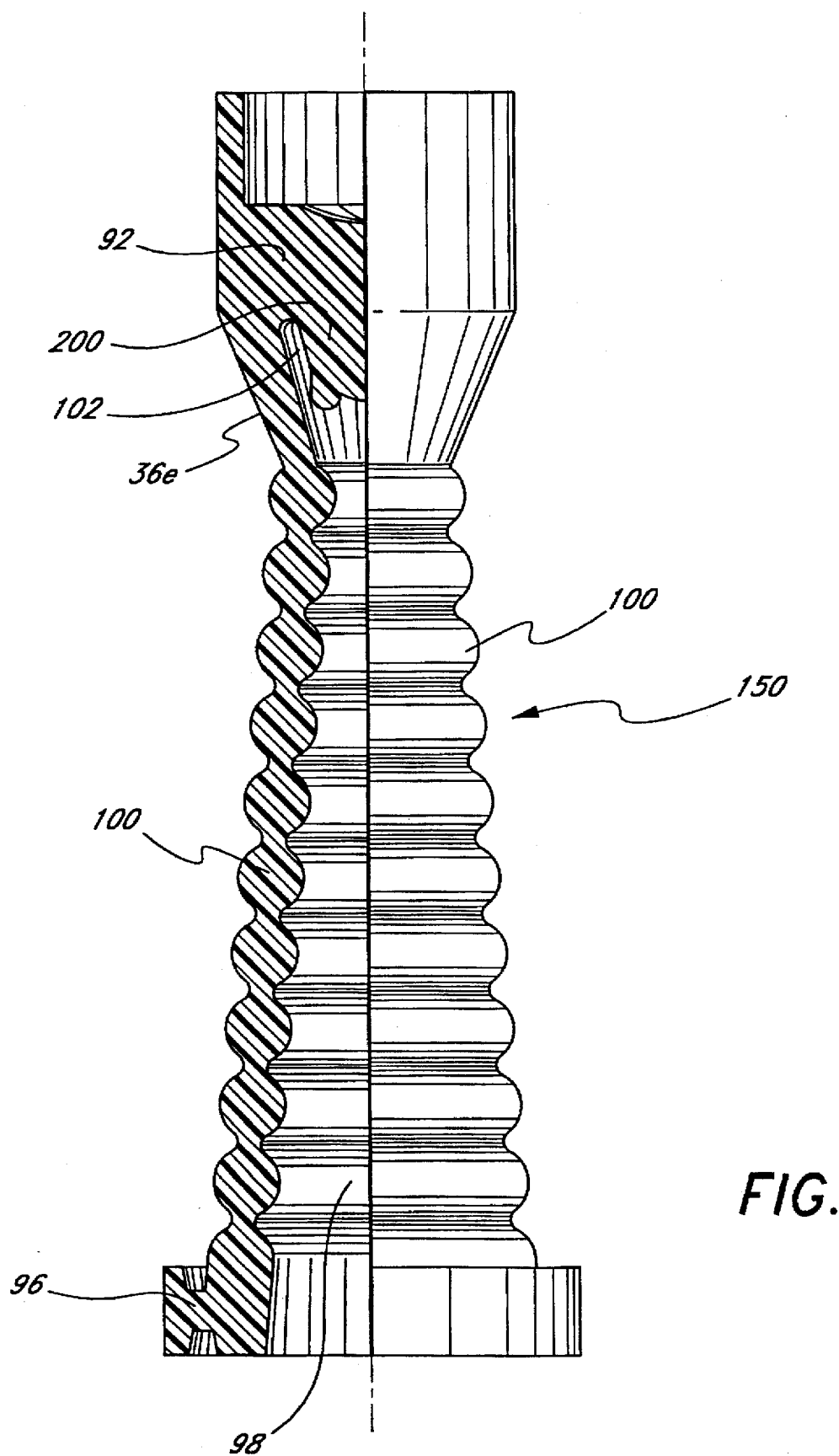
FIG. 15 is a longitudinal partial cross-sectional view of a still further embodiment of the seal of this invention.
Figure 16:
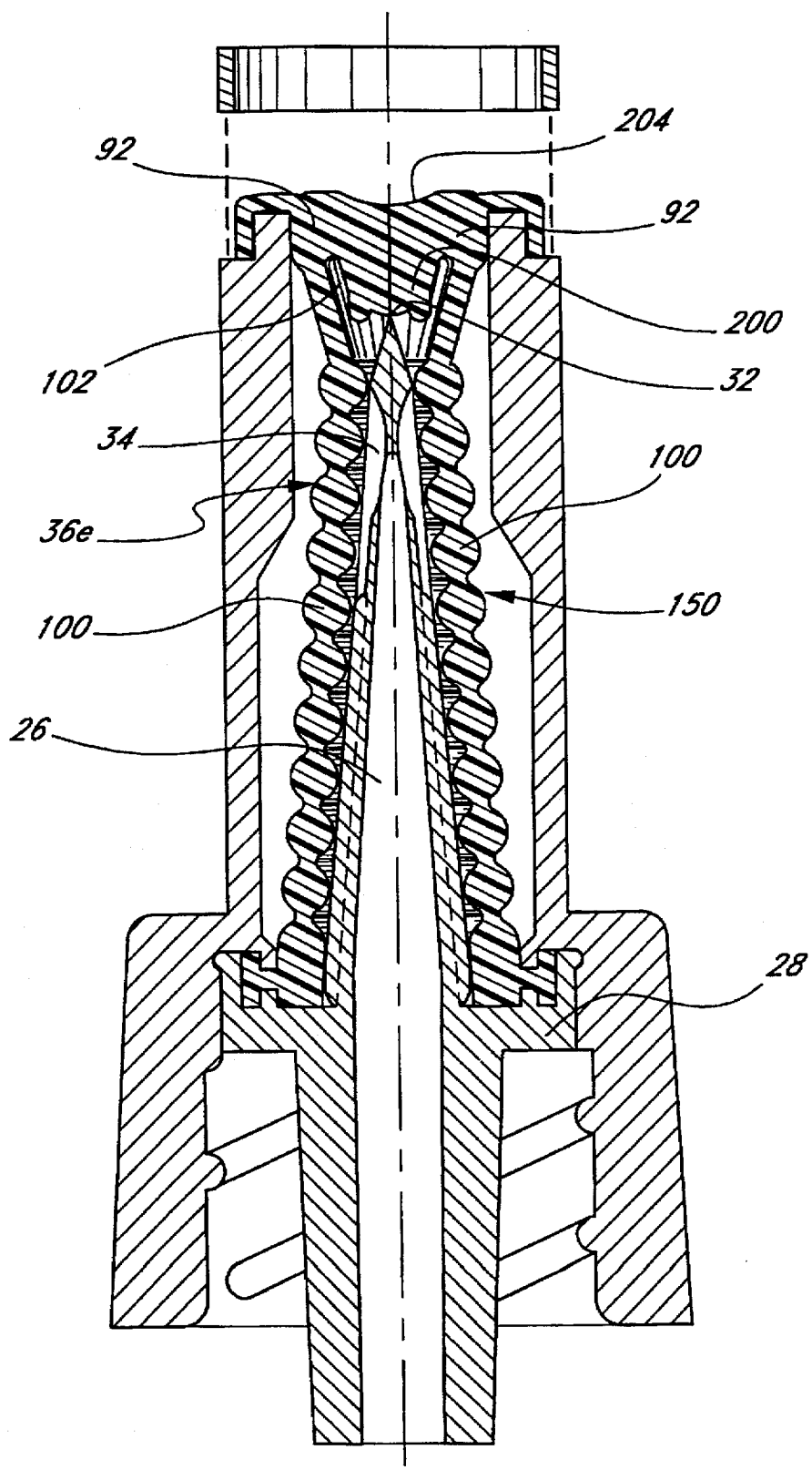
FIG. 16 is a longitudinal cross-sectional view, after assembly, of the valve shown utilizing the seal of FIG. 15.
Figure 17:
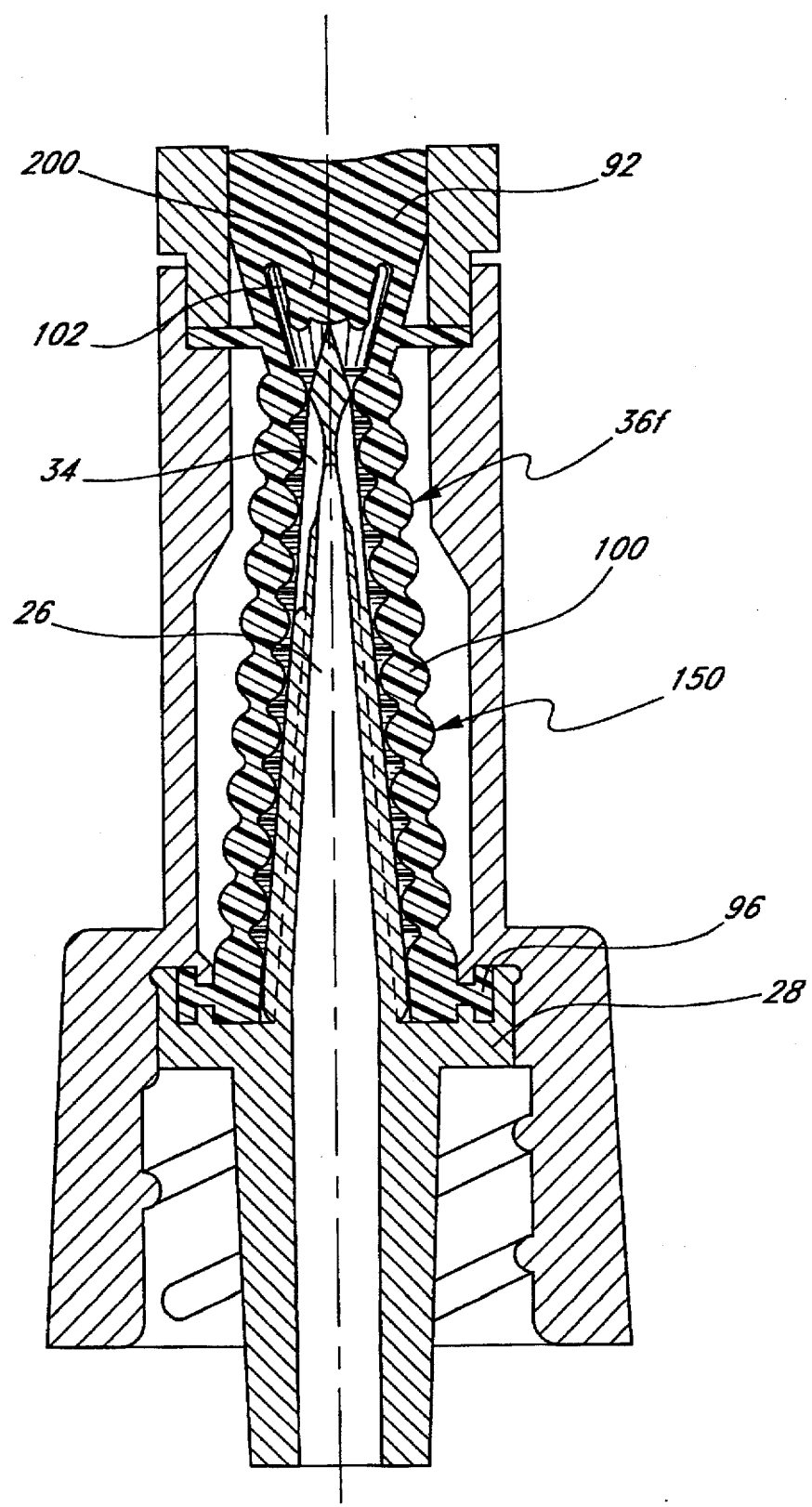
FIG. 17 is a longitudinal cross-sectional view, after assembly, of the valve shown utilizing still another embodiment of the seal.
Figure 18:
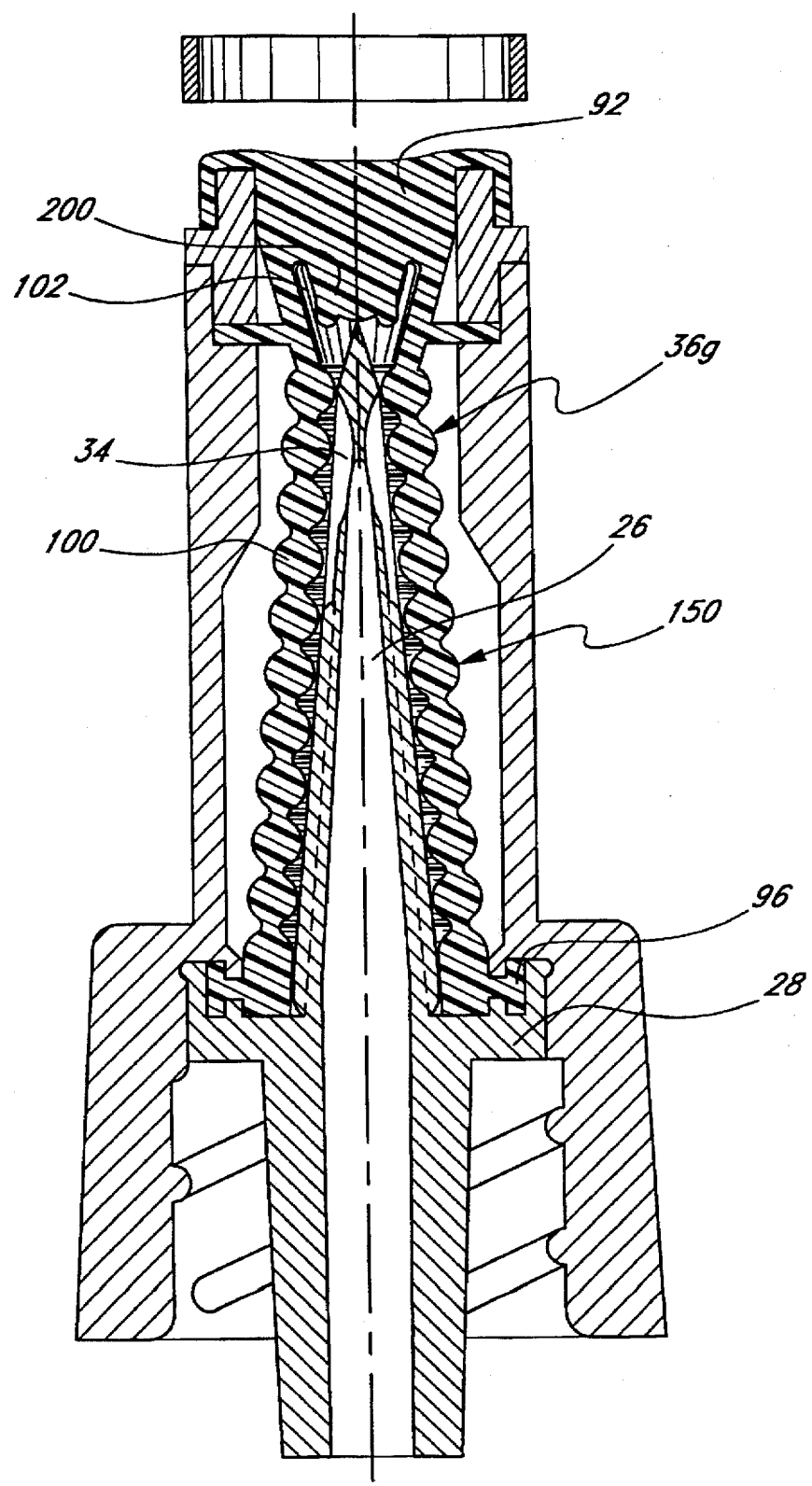
FIG. 18 is a longitudinal cross-sectional view, after assembly, of the valve utilizing yet one more embodiment of the seal.
Figure 19:
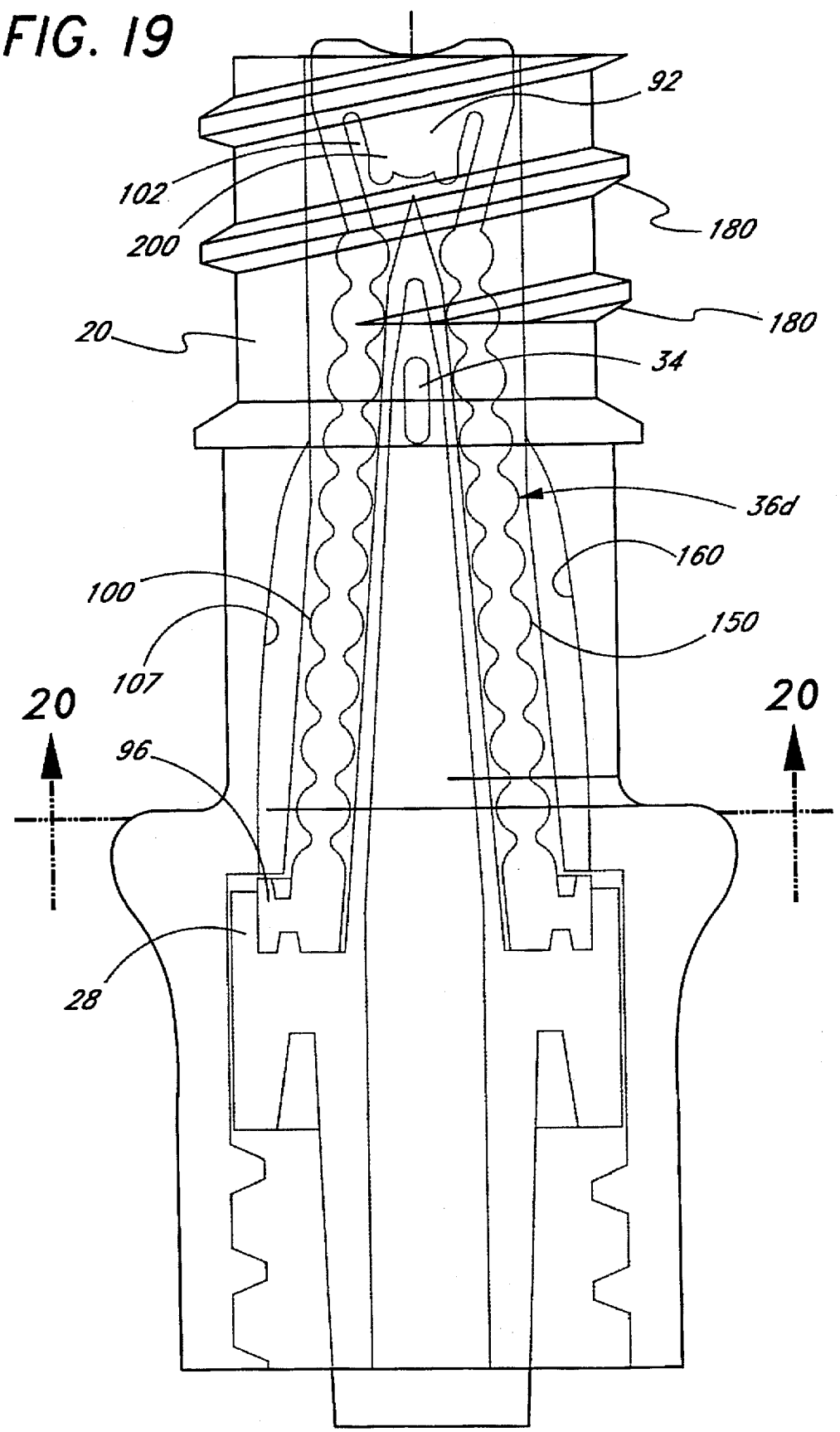
FIG. 19 is a side elevation view, after assembly, of the seal and spike shown in FIG. 14 connected to the body or housing shown in FIGS. 20 and 21.
Figure 20:
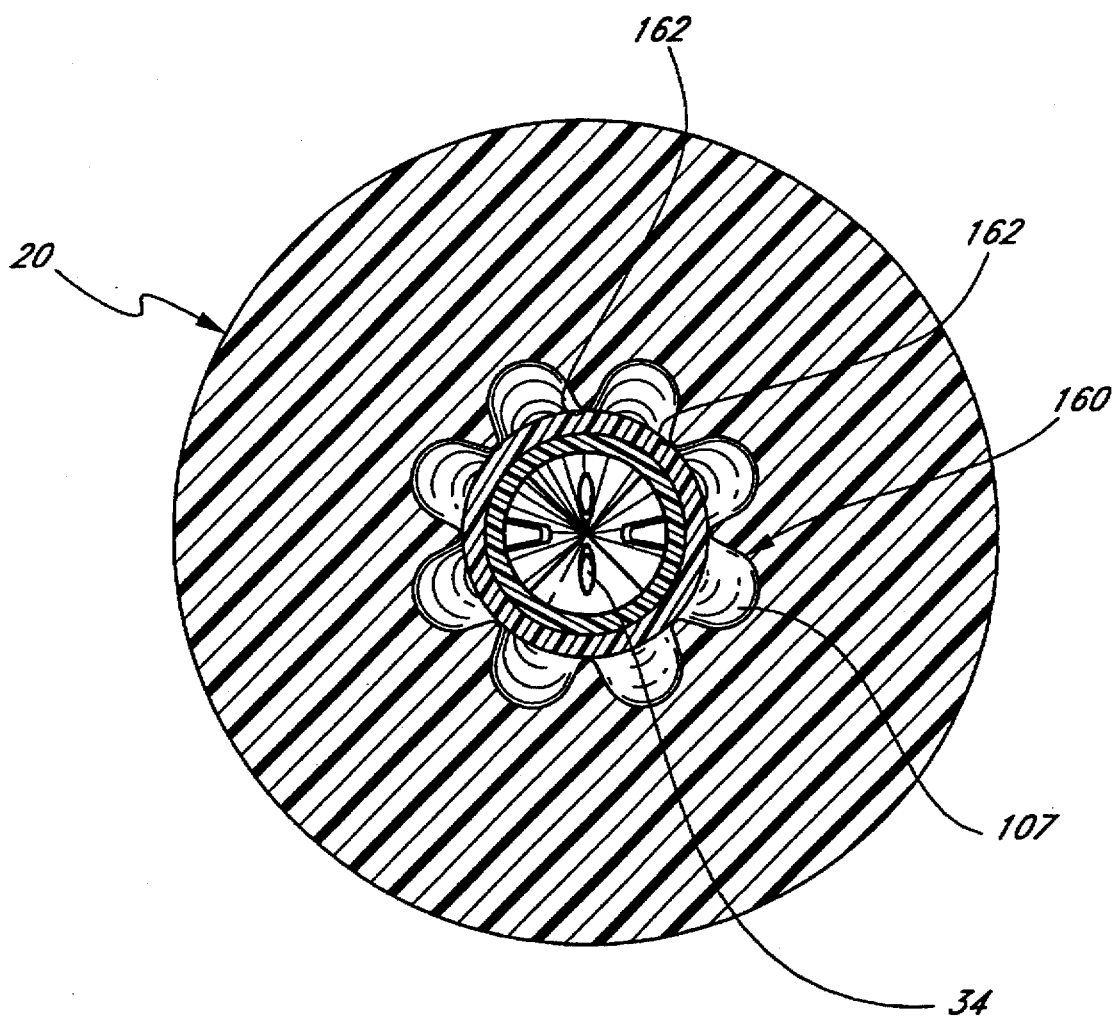
FIG. 20 is a cross-sectional view taken along line 20—20 of FIG. 19.
Figure 21:
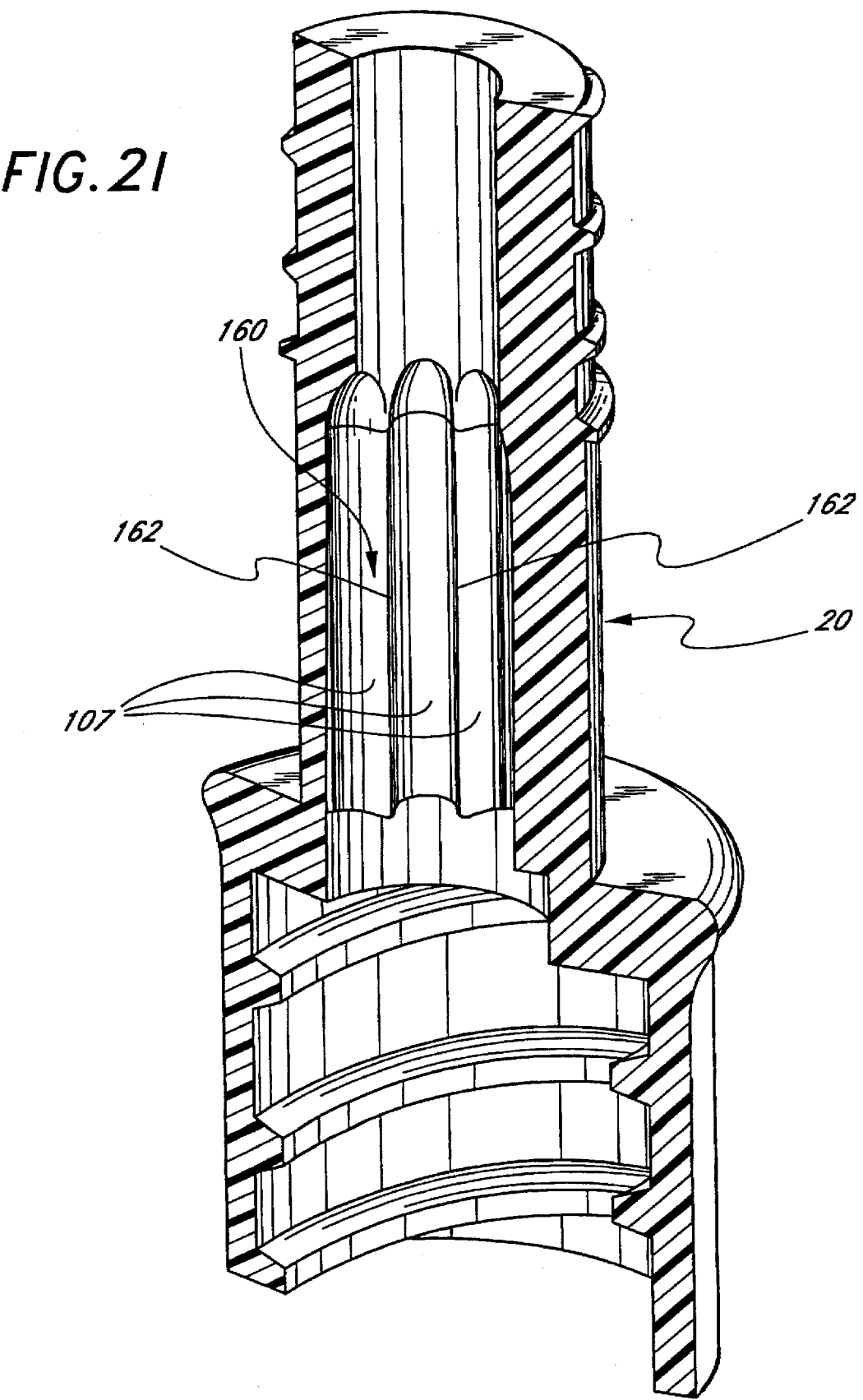
FIG. 21 is a perspective view of the housing shown in FIG. 19, with sections broken away to show the wall structure of the cavity containing the seal shown in FIGS. 13 and 14.

As mentioned above, preferably the seal 36d has a precut slit 11 in the cap 92 lying along the longitudinal axis of the valve 10. The seal cap 92 has a unique configuration that insures that the slit 11 closes and is sealed upon withdrawal of a syringe (not shown) and reformation of the seal 36d. It includes an enlarged, internal, pressure responsive member 200 which is integral with the seal cap 92. Between the proximal end of the side wall 150 and the member 200 is an annular space 102 which is filled with the fluid in the cavity 98. This fluid is under pressure, for example at the blood pressure of the patient to which the valve 10 is attached. Referring to FIG. 14, fluid, for example the patient's blood, flows through the holes 34 in the spike 26, filling the cavity 102. This fluid presses against the exterior of the member 200, closing the slit 11 when the seal is decompressed as shown in FIGS. 14 and 19. The pressure from this fluid creates a high pressure seal which prevents fluid from escaping valve 10 through the slit 11. There is a semi-cylindrical annular flange tear ring 104 on the end of the member 200 which advantageously extends the useful life of the seal 36d.

Preferably, there is a tear ring 104 integral with the member 200 along the perimeter of the internal surface the member 200, and a slight saucer-like depression 204 in the external surface of the seal. The pressure responsive element in the decompressed state closes any orifice in the seal 36d to provide an essentially fluid-tight seal while in the decompressed state. The pressure responsive member 200 enables the valve to maintain a fluid-tight seal even at very high pressures sometimes experienced in medical applications, particularly when the valve 10 is connected to a patient's artery. The center of the member 200 and the annular space 102 are coaxial with the entryway 11a to the orifice 11. The pressurized fluid fills the annular space 102 to apply pressure that compresses the member 200 to tightly close the entryway 11a to the orifice 11. In a preferred valve embodiment the distance from the entryway 11a to the proximal end of the seal cap 92 is from 0.500 to 0.075 inches and more preferably approximately 0.100 inch.

Figure 22:
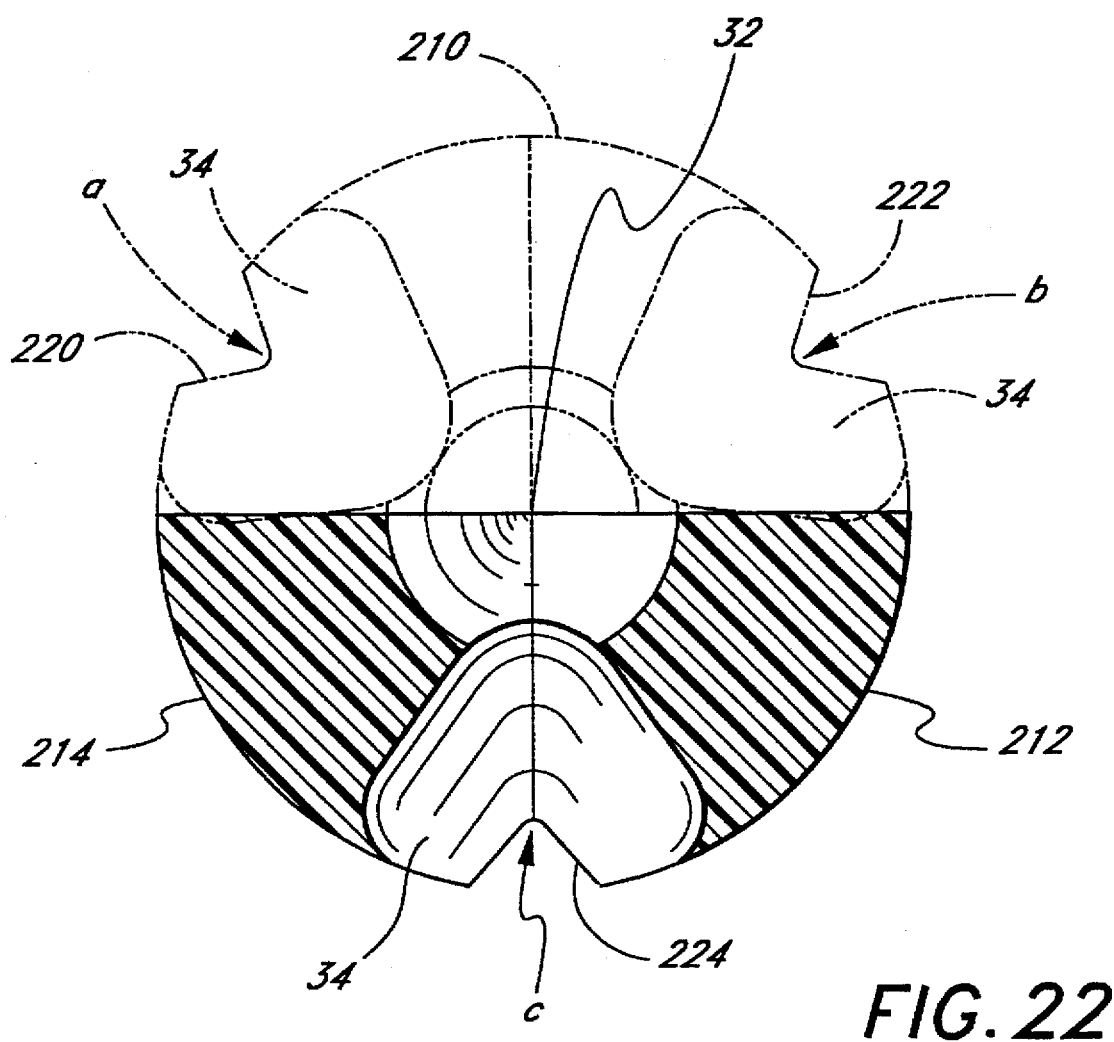
FIG. 22 is a greatly enlarged, cross-sectional view taken along line 22—22 of FIG. 14.

As best illustrated in FIG. 22, the tip 32 is designed to avoid tearing the seal. The tip 32 has three facets 210, 212, and 214 which are joined with each other along parting lines a, b, and c. This junction of the facets 210, 212, and 214 frequently is ragged and will tear the seal 36d. This is prevented by the parting lines a, b, and c, or junctions, being disposed within recesses 220, 222, and 224, respectively, to provide "buried parting lines."

Another alternative embodiment of the valve 10 using the seal 36d is shown in FIG. 8 and FIGS. 19 through 21. In this embodiment, the inner wall 160 of the upper end of the conduit 20 is provided with at least one, and preferably, a plurality of radial indentations 107. The indentations 107 are elongated and disposed generally parallel to the longitudinal axis of the valve 10 in a symmetrical, star-like configuration. Each indentation has opposed lateral edges 162 which engage the seal 36d upon compression of the seal 36d. The indentations provide space into which the seal 36d expands upon compression.

Figure 23:
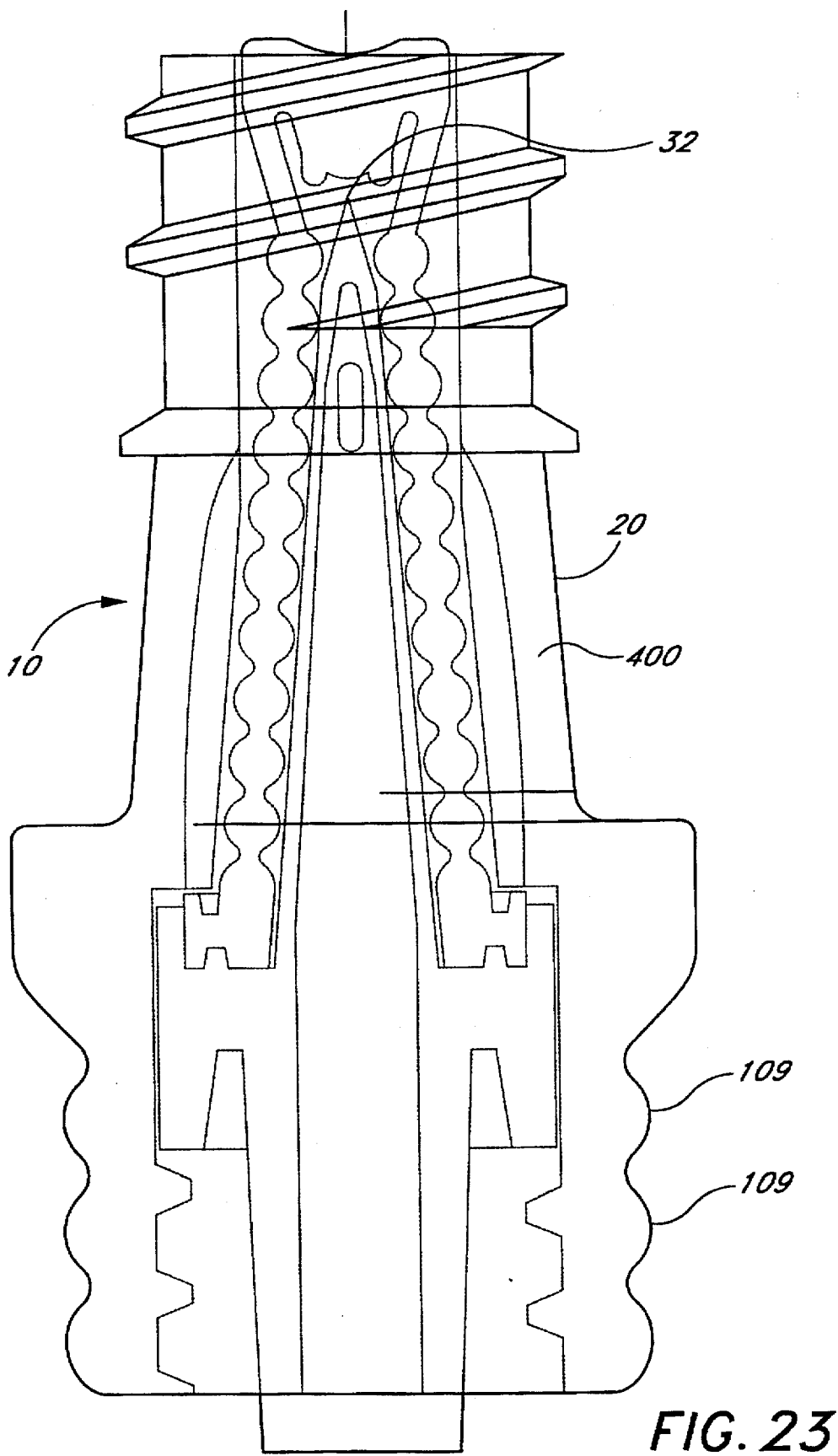
FIG. 23 is a side elevation view, after assembly, of the seal and spike shown in FIG. 14 connected to another alternative embodiment of the housing.
Figure 24:
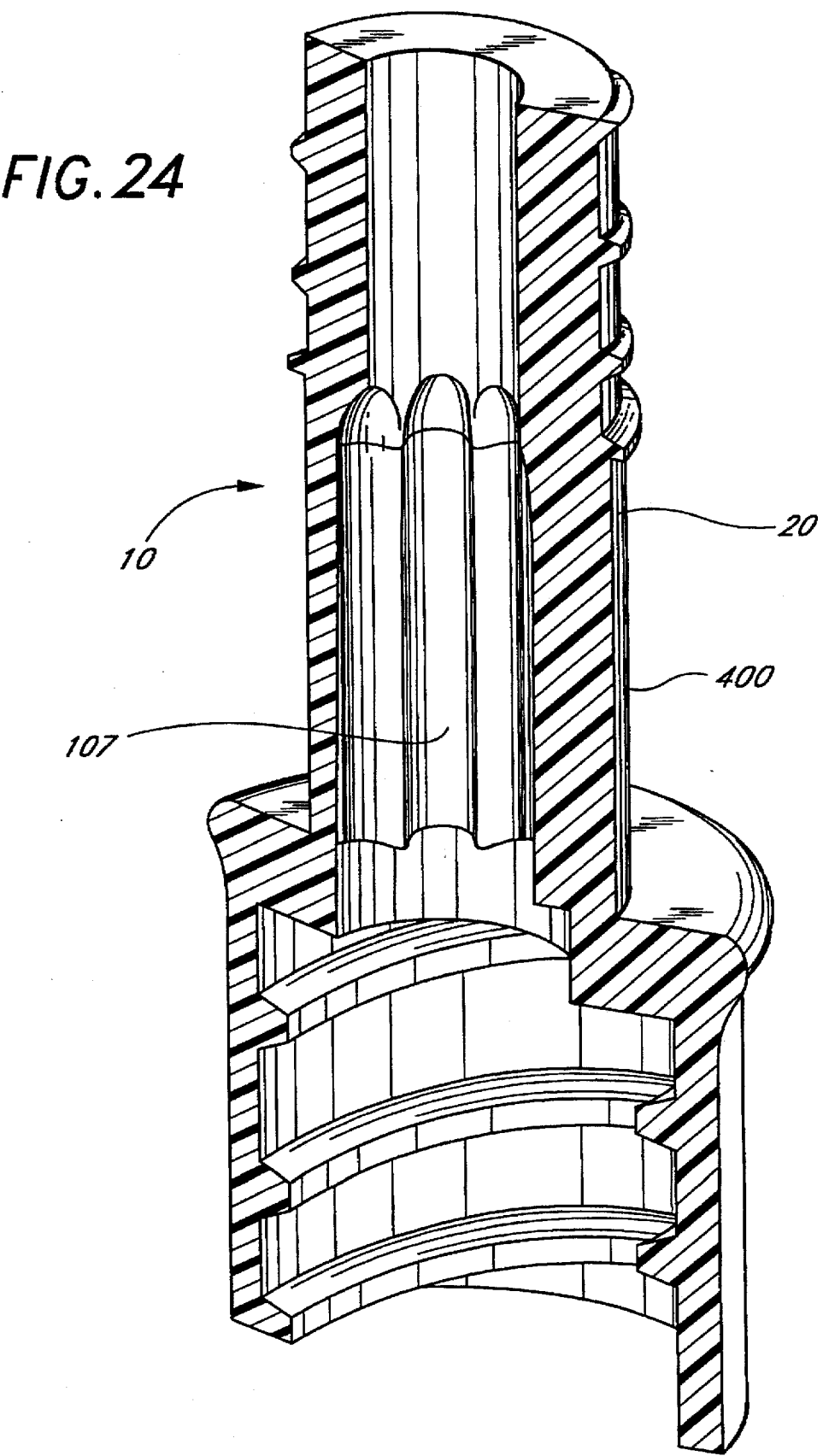
FIG. 24 is a perspective view of the housing shown in FIG. 23, with sections broken away to show the wall structure of the cavity containing the seal shown in FIGS. 13 and 14.

Another alternative embodiment of the valve 10 using the seal 36d is shown in FIGS. 23 and 24. In this embodiment, the distal end 400 of upper conduit 20 comprises a truncated conical shape.

Figure 25:
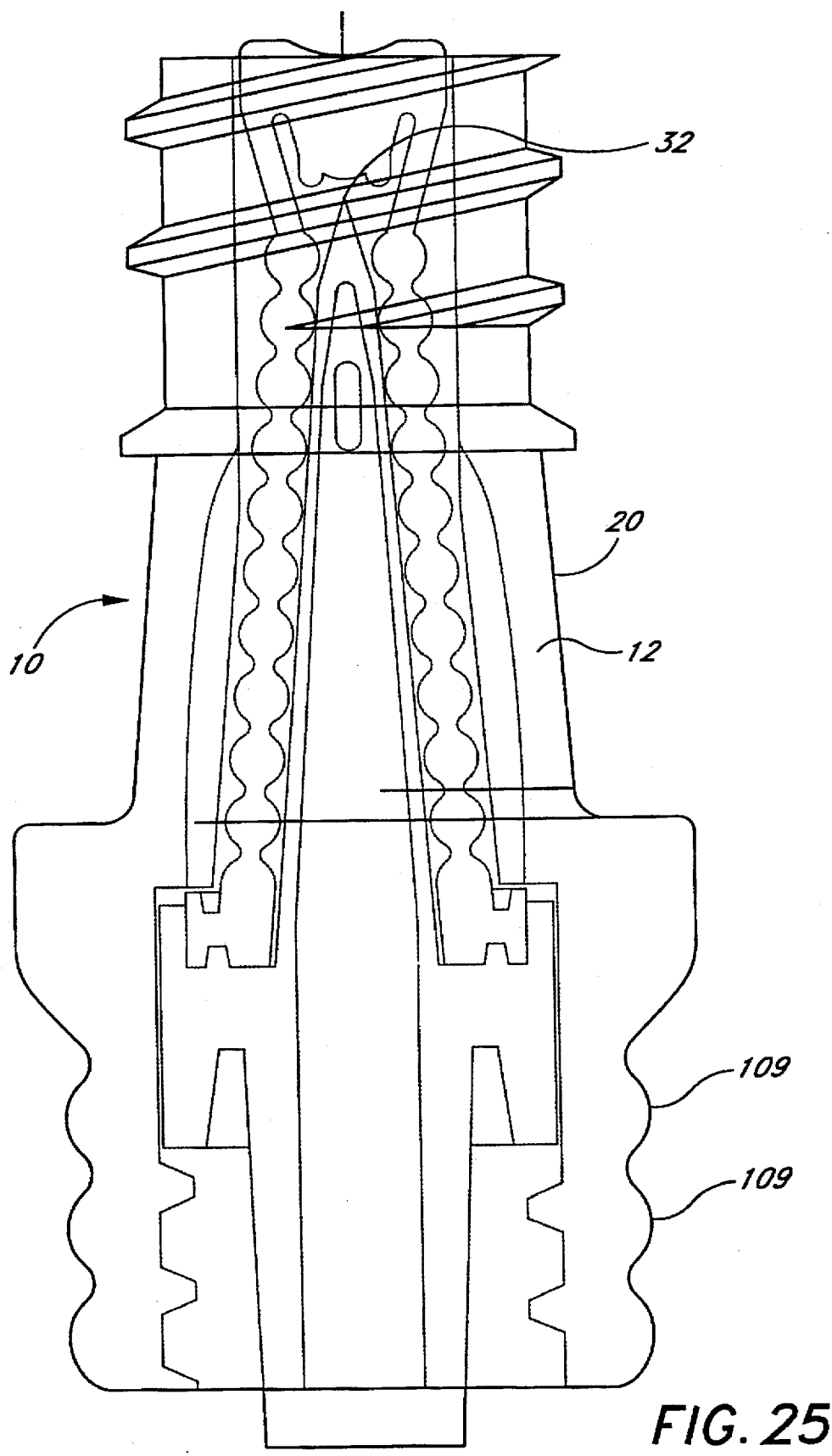
FIG. 25 is a side elevation view, after assembly, of the seal and spike shown in FIG. 14 connected to another alternative embodiment of the housing.

Another alternative embodiment of the valve 10 is shown in FIG. 25. In this embodiment, the distal end of the housing 12 is provided with at least one raised gradually sloping ridge 109 in order to facilitate handling of the valve 10 by a healthcare worker. The ridges 109 help prevent the valve 10 from slipping from between the fingers of a healthcare worker.

Figure 8:
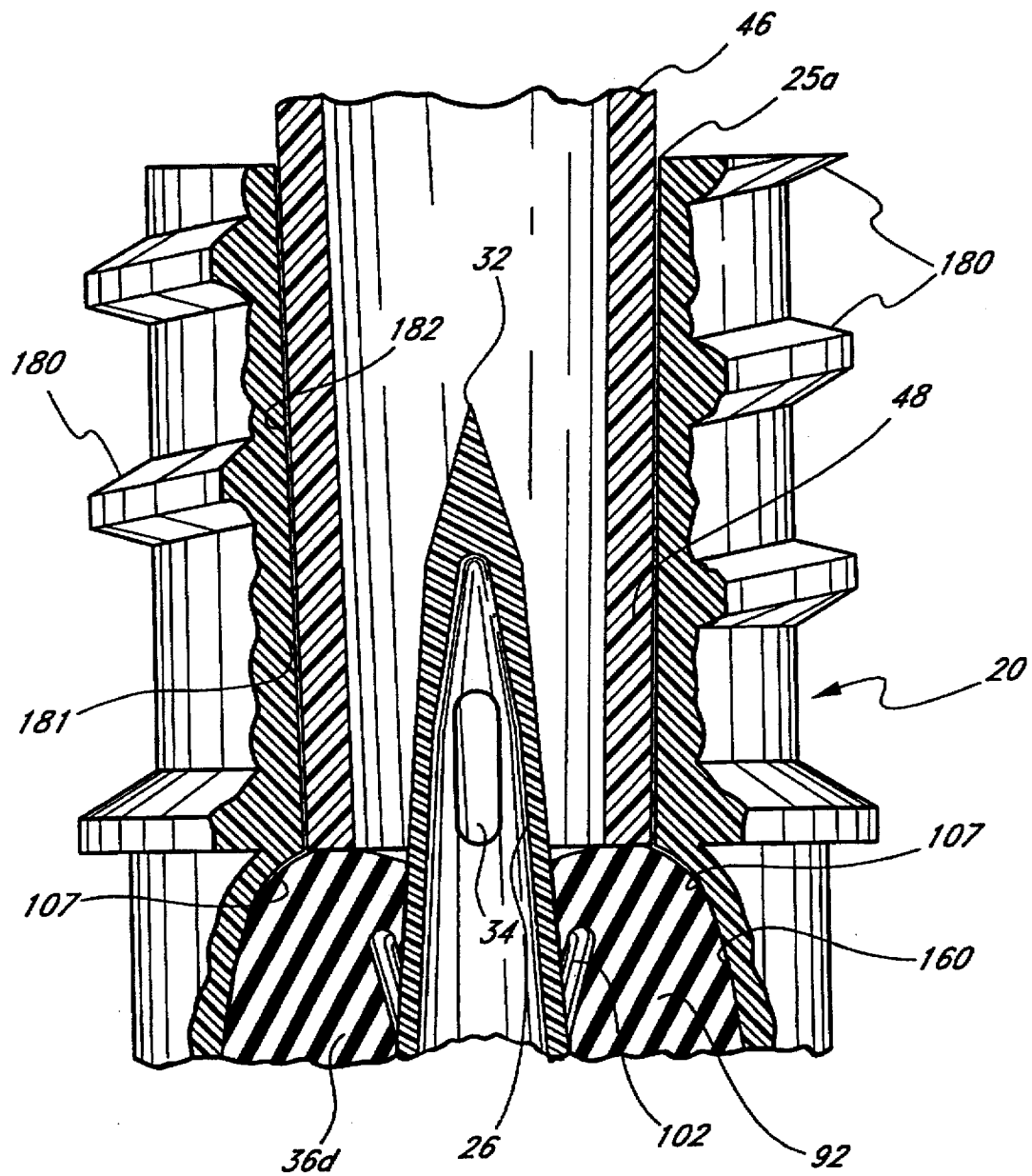
FIG. 8 is a schematic illustration of an ANSI delivery end of a medical implement compressing the seal of a valve.

As best shown in FIG. 8, the wall 181 of the proximal end of the upper conduit 20 is tapered inward at the same angle as the nose 48 of the syringe 46. In accordance with ANSI standards, the taper is 0.006 inch per linear inch. The wall 182 of the syringe nose 48 bears against the wall 181 as the nose slides into the opening 25a to push the seal 36d inward compressing it and forcing the tip 32 of the spike 36 to enter the slit 11. The seal 36d expands upon compression to fill essentially completely the upper portions of the indentations 107. Some sections of the seal 36d are wedged between the edges 162 and other sections fill the indentations 107. As the liquid flows through the nose 48 through holes 34, air in the nose 48 is forced out of the nose 48 and expelled from the valve 10 between the walls 181 and 182. Thus, essentially the entire prescribed dosage is delivered through the valve 10 to the patient. Fluid flows through the through-holes 34, but does not leak between either the seal 36d and the wall 181 or between the abutting walls 181 and 182.

FIGS. 15, 16, 17, and 18 depict embodiments of seals, namely, seal 36e, seal 36f, and seal 36g, which are substantially the same as the seals 36a (FIG. 10), seal 36b (FIG. 11), and seal 36c (FIG. 12), except the side wall 150 employing the circular tires 100 is used in place of the accordion wall portion 94.

Other components of the valve interact with the various embodiments of the seal in a similar fashion to their interaction with seal 36 of FIG. 2. Prior to use of the valve 10, it is preferable that the seal caps 40 or 92 be pierced centrally by a steel needle in the axial direction, precutting the seal to provide the slit 11 in order to allow for more rapid decompression and reformation of the seal upon piercing by the spike 26. The seals are advantageously formed from a material which can repeatedly reseal and prevent fluid from flowing around the seal material. The seal 36 should also be capable of being forced down and then spring back into position to reseal the valve. Material that is too soft will not reseal effectively; however, will not be capable of springing back after opening of the valve. Material that is too hard will provide sufficient spring force; however, will not effectively seal. Thus, in a preferred embodiment, the seal is formed from a silicone having a hardness in the range from 30–70 Shore durometer units, and more preferably in the range 40–50 Shore durometer units. A cure silicone polymer in the preferred hardness range is available from Wacker Silicone Corp. of Adrian, Mich. In some valve embodiments, it is desirable to provide additional lubricity to the seal 36 to allow it to spring back and reseal more effectively. Dow Chemical Co. produces a silicone formulation with silicone oil built in to provide this additional lubricity.

In general, the closing of the valve 10 is provided not by the side wall of the seal 36 which immediately covers the through-holes 34, but by the seal cap 40, or seal cap 92 filling the proximal end of the cavity 98 and the opening 25a. Thus, the seal caps 40 and 92 are sufficiently thick to reseal the opening 25a effectively after valve closure. However, the seal caps 40 and 92 should also be sufficiently thin to allow them to readily return to the closed position. Preferably the thickness of the caps 40 and 92 ranges between 0.075 and 0.500 inch and more preferably may be approximately 0.100 inch.

The valve can be provided in a sterile and disposable form such that after its use in a given installation is exhausted, the device is discarded. However, as described above, in any given installation, the valve can be reused multiple times. Since the valve does not employ needles, there is little chance that the device will inadvertently cause skin puncture. Therefore, the extra precautions required for handling and disposing of needles is obviated. It will be apparent from the detailed description provided herein that the valve can provide for the elimination of nearly all needles used in the medical environment. With the use of the valve described above, the need for all needles except those that are directly input into a patient is, advantageously, eliminated.

The valve 10 is used to provide a closed, patient access system for transferring a predetermined amount of medication from a remote source to the patient. The valve 10 is connected by the distal end to the patient, for example, a vein or artery in fluid communication with the valve. Blood fills the valve, but the seal 36d, for example, prevents any blood from leaking from the valve. The delivery end or nose 48 of the medical implement is inserted into the valve as depicted in FIG. 8, pushing the nose 48 against the seal to compress the seal sufficiently to allow the tip 32 of the spike 24 to pierce the seal and enter said delivery end. The predetermined amount of medication in its entirety may now be transferred through the nose 48 into the valve 10 and into the patient. Since the nose 48 and seal 36d engage in a manner so that the tip 32 of the spike element 24, upon piercing the seal, meets the seal to avoid formation of any dead space at the interface between nose 48 and the seal surface 40b. Transfer directly through the valve 10 of essentially the entire predetermined amount of medication from the syringe 46 to the patient, so that essentially none of said predetermined amount is collected in any dead space in the valve, is accomplished. Upon withdrawing the nose 48 from the valve 10 the seal 36d returns to the decompressed state to close the valve and maintain while in said decompressed state a fluid tight seal even at high pressures and after repeated uses.

MEDICAL IMPLEMENT INDICATOR

In order to preclude the effects of the psychological disorder referred to as Intensive Care Unit Psychosis and to avoid endangering the ability of patients to recover from their ailments by having their sleep interrupted when healthcare workers turn on the lights to locate and manipulate medical implements for the administration of fluids, such as medications, a medical implement indicator is provided. The medical implement indicator allows a healthcare worker to enter a dark environment and find and keep track of a medical implement by locating and following a light emitting source that is associated with the medical implement. The source of light emission may constitute any of a number of devices and materials that are attached to or otherwise incorporated into the medical implements, so long as the medical implements are thereby indicated in the dark.

The medical implement indicator of the present invention may take the form of any of a wide variety of shapes and sizes in order to be used with virtually any medical implement as defined hereinabove. The indicator of the invention can be used in connection with any of a multitude of medical implements, including those described herein, as well as other well-known medical connectors, adapters, and valves, such as, e.g., the CLICK LOCK® and PIGGY LOCK® medical connectors offered by ICU Medical, Inc. located in Irvine, Calif. In addition, the medical implement indicator can be used in association with many other products offered by a diversity of manufacturers.

The indicator provided by the present invention includes among its features the indicating in the dark of the medical implement to which it is affixed. Such an indication is mediated by the emission of light that may thereby be detected by those such as medical personnel who have as their responsibility the exploitation of the medical implements for the administration of fluid-type drugs and other fluids to patients. Light may be emitted from all kinds of sources so as to perceived as visible, and those devices and materials that emit such light while being in association with the medical implements of the present invention form its several embodiments. Examples of such light emitting materials and devices include phosphorescent materials, fluorescent materials, light emitting diodes (LEDs), tungsten containing devices (e.g., light bulbs), etc. It is preferred that the indicator be comprised of a material or device that "glows in the dark." That is, indicators may be rendered luminescent by virtue of agents that through off light resulting from excitation even after the excitation has ceased. Such agents may be organic or inorganic, naturally occurring or synthetic, and may include phosphors and the like; all are encompassed within the scope of the invention.

The light emitting devices and materials provided by prevent invention are to be affixed to the medical implements indicated thereby using any manner of affixation that is conventional and known to those in the art. For example, the light emitting material may be impregnated into the substance forming all or a part of the medical implement itself. Alternatively, a device may be light emitting by virtue of the material it contains rendering it functional upon association with the subject medical implement. Such devices include light emitting tape, light emitting paint, LED displays, and battery operated light bulbs, etc. Other devices coming within the scope of the invention include annular rings, particularly glow rings, which may or may not be built into the medical implements to be indicated as set forth below.

Figure 26:
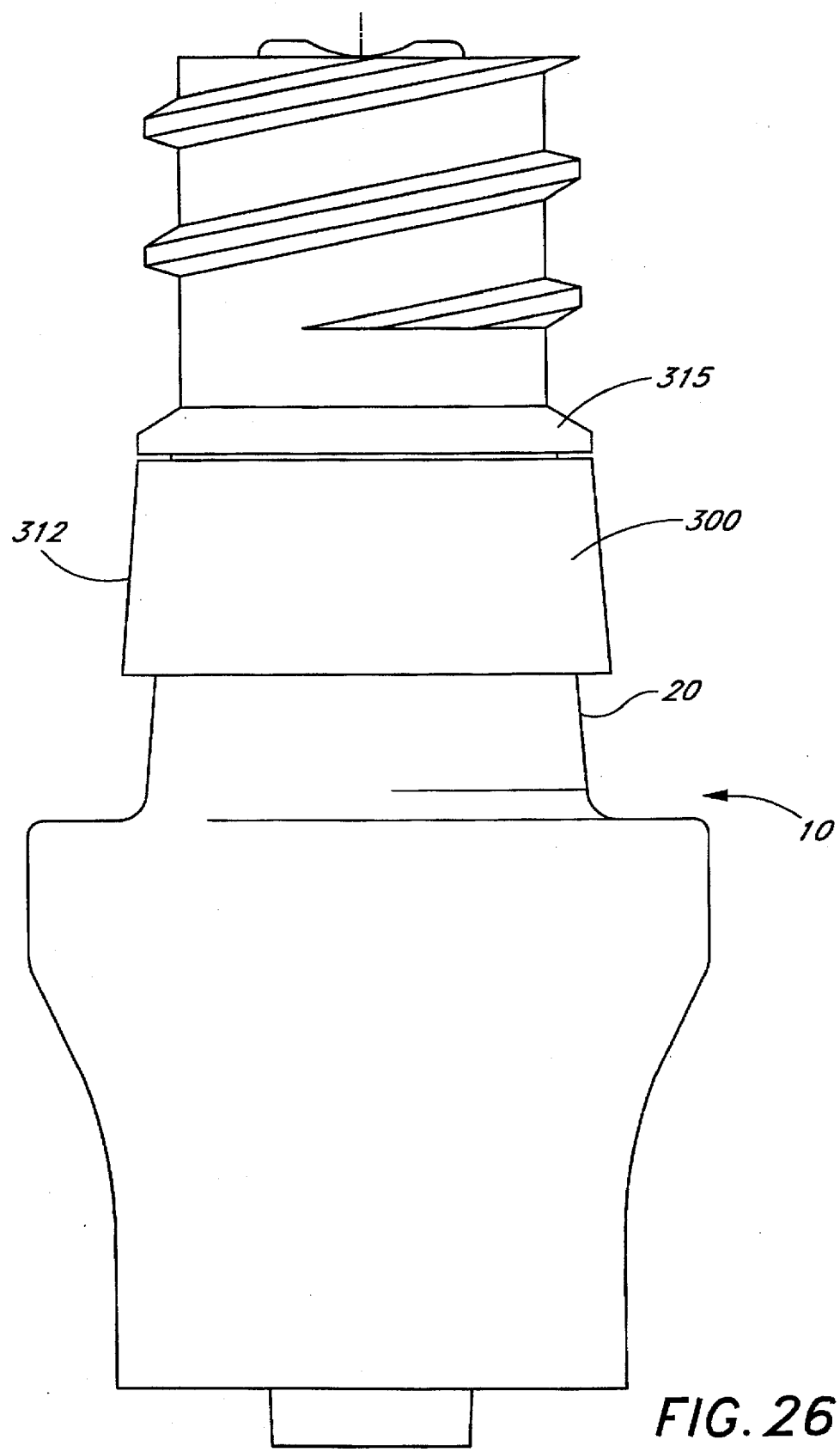
FIG. 26 is a side elevation view of the housing shown in FIG. 23 shown in connection with the medical implement indicator shown in FIG. 30 of the present invention.
Figure 30:
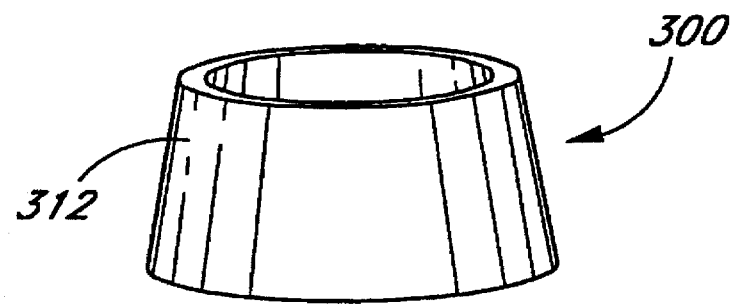
FIG. 30 is a perspective view of an alternative embodiment of the medical implement indicator of the present invention.

FIGS. 26 and 30 illustrate one preferred embodiment of the member comprising the medical implement indicator 300 of the present invention. Preferably, the medical implement indicator 300 is an annular ring made from a plastic material that maintains a fit with the valve 10 discussed above or other medical implement. Preferably, a phosphorescent material is incorporated within the medical implement indicator 300 and this material absorbs light when the indicator 300 is situated in a lighted environment and emits the light that is absorbed when the indicator 300 is positioned in a dark environment. Desirably, after being present in a lighted environment for at least twelve hours in order to absorb sufficient light, the medical implement indicator 300 will emit light in a dark environment for up to twelve hours.

Figure 27:
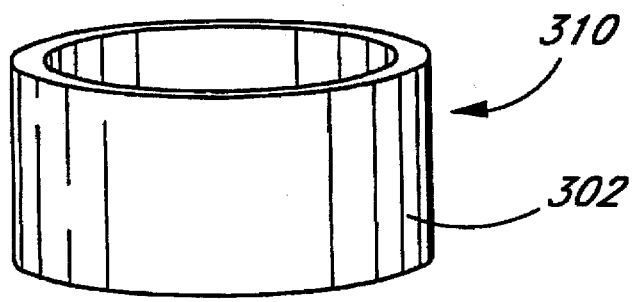
FIG. 27 is the first embodiment of the medical implement indicator of the present invention.
Figure 28:
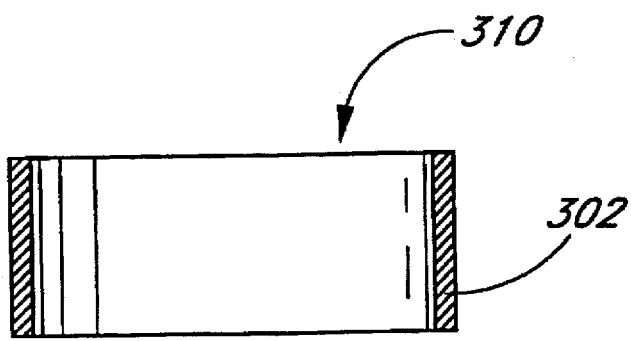
FIG. 28 is a longitudinal cross-sectional view of the medical implement indicator of FIG. 27.

An alternative embodiment of the indicator 310 is illustrated in FIGS. 27 and 28. The walls 302 of the annular ring are parallel and of equal thickness. The walls 302 of the medical implement indicator 310 can be of any thickness as long as the indicator 310 is able to encircle a medical implement. Preferably, the walls 302 are not so thick as to hamper the connection of two medical implements. Further, the walls 302 should not be so thin as to be unable to absorb sufficient light to emit a strong enough glow in a dark environment.

As will be recognized by one of skill in the art, the width of the medical implement indicator 310 can be of varying sizes depending on the type of medical implement it indicates. The width of the indicator 310 should be of sufficient width to indicate a medical implement in a dark environment. The width of the medical implement indicator 310 should not be so small as to be overlooked in a dark room. However, the width of the medical implement indicator 310 should not be so large as to interfere with the connection of the two medical implements.

The medical implement indicator 300 is preferably manufactured alone and then placed on a medical implement. In this embodiment, the installation of the medical implement indicator 300 can be performed by healthcare workers themselves. The advantage of providing installation by a healthcare worker is that the medical implement indicator 300 can be used to retrofit traditional medical implements in their current environment without requiring the repurchase of medical implements with a medical implement indicator 300 already installed. Alternatively, the assembly of the medical implement indicator 300 to a variety of medical implements may be performed by the manufacturer to save the healthcare worker from performing the assembly process.

The medical implement indicator 300 is designed to be easily placed onto any medical implement, but difficult to remove. Referring to FIG. 26, an annular retaining ridge 315 is included on a medical implement 10 to hold the indicator 300 in place. Advantageously, the medical implement indicator 300 is pressed over the retaining ridge 315 as it is placed on the medical implement 10. During assembly, the indicator 300 stretches slightly to fit over the retaining ridge 315 and then returns to its original shape once it is in place. The retaining ridge 315 acts as a physical barrier to prevent removal of the medical implement indicator 300 during normal use of the medical implement 10 upon which it is installed. If an annular retaining ridge 315 is not provided on the medical implement, the medical implement indicator 300 may be appended to the medical implement by any one of a number of methods known to one of skill in the art including, but not limited to, pressure fit or other mechanical connection, heat sealing, glue, pressure lock, bonding or the like.

The medical implement indicator 300 can be placed on a variety of medical implements as described above. Two preferred implements are the CLICK CLOCK® and PIGGY LOCK® connectors which are manufactured by ICU Medical, Inc., the assignee of this patent application.

FIGS. 26 and 30 illustrate another preferred embodiment of the medical implement indicator 300. In this embodiment of the indicator 300, the walls 312 of the indicator 300 are tapered in a conical shape. This embodiment of the indicator 300 is preferred for use with certain medical implements, such as the valves 10 shown in FIGS. 23 through 26, in which the upper conduit 20 is tapered in a conical shape. Preferably, the taper of the walls 312 of the medical implement indicator 300 is equivalent to the taper of the upper conduit 20 of the valve 10. The taper of the indicator 300 enables a snug fit of the medical implement indicator 300 with the valve 10.

Figure 29:
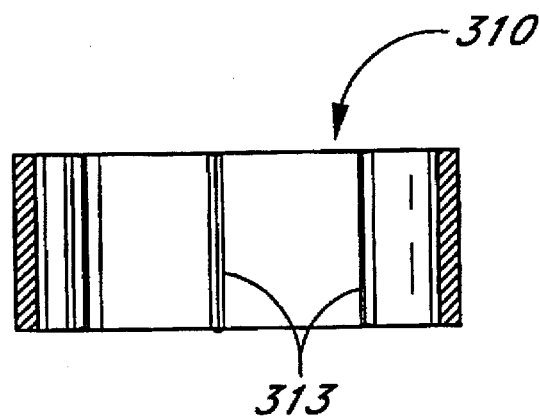
FIG. 29 is a longitudinal cross-sectional view of the medical implement indicator of FIG. 27 utilizing interior ridges.

FIG. 29 illustrates another preferred embodiment of the medical implement indicator 310 of the present invention. The indicator 310 of this embodiment is similar to the indicator shown in FIGS. 27 and 28. Advantageously, vertical ridges 313 are provided on the interior surface of the medical implement indicator 310 to provide for an pressure fit with a medical implement, such as a valve (not shown). Although the ridges 313 are shown parallel to each other in the vertical direction, it is contemplated by the present invention that the ridges 313 may be disposed in any direction relative to each other and need not be vertical, parallel or straight.

In a similar fashion to the medical implement indicator 300 shown in FIG. 26, the medical implement indicator 310 shown in FIGS. 27–29 may be spaced on the upper conduit 20 of a medical implement such as a valve 10 (see FIGS. 1, 2 and 10). The medical implement indicator 310 may be held in place by the locking ears 22 of FIG. 1, or, referring to FIG. 19, an annular ridge 314 distal the threads 180 may be used to hold the medical implement indicator 310 in place.

Some embodiments of the medical implement indicator are preferably prepared from a plastic material, such as polypropylene, but it is additionally contemplated that the connection indicator could be prepared from other medically inert materials known to those of skill in the art. The light emitting component may be provided by the addition of a zinc sulfide material to the polypropylene. Preferably, the zinc sulfide material is mixed with the polypropylene to constitute about 25% to about 50% of the zinc sulfide and polypropylene containing mixture. If the zinc sulfide material and polypropylene material are mixed in equal parts, i.e., 50% zinc sulfide and 50% polypropylene, the light emitted from the medical implement indicator will be very bright and will last for well in excess of eight hours. The zinc sulfide material is very expensive, approximately forty-five times the cost of polypropylene. It is consequently desirous to use as little zinc sulfide material as possible to achieve the desired intensity and duration of illumination. Preferably, a sufficient percentage of the zinc sulfide material is used in combination with the polypropylene to provide a sufficient luminescence so that the medical implement indicator is detectable in a dark environment and will glow continuously for approximately eight to ten hours. In one preferred embodiment, approximately 30% of the material used to form the medical connection indicator is zinc sulfide while the remainder is polypropylene.

The medical implement indicator has been described above as an annular ring shape, however, the medical implement indicator should not be considered as only being an annular ring. The medical implement indicator need only be annular in shape when the medical implement is cylindrical, and, further, need not have an "O-shape," but may instead have a "C-shape." One of skill in the art will recognize that the shape of the medical implement indicator can be adapted to suit the shape of any type of medical implement. For example, if the medical implement utilizes a hexagonal shape, as in a conventional hexagonal nut type connector, the medical implement indicator may be formed of a shell with a hexagonal shape in a radial cross-section instead of an annular shape in radial cross section.

Figure 31:
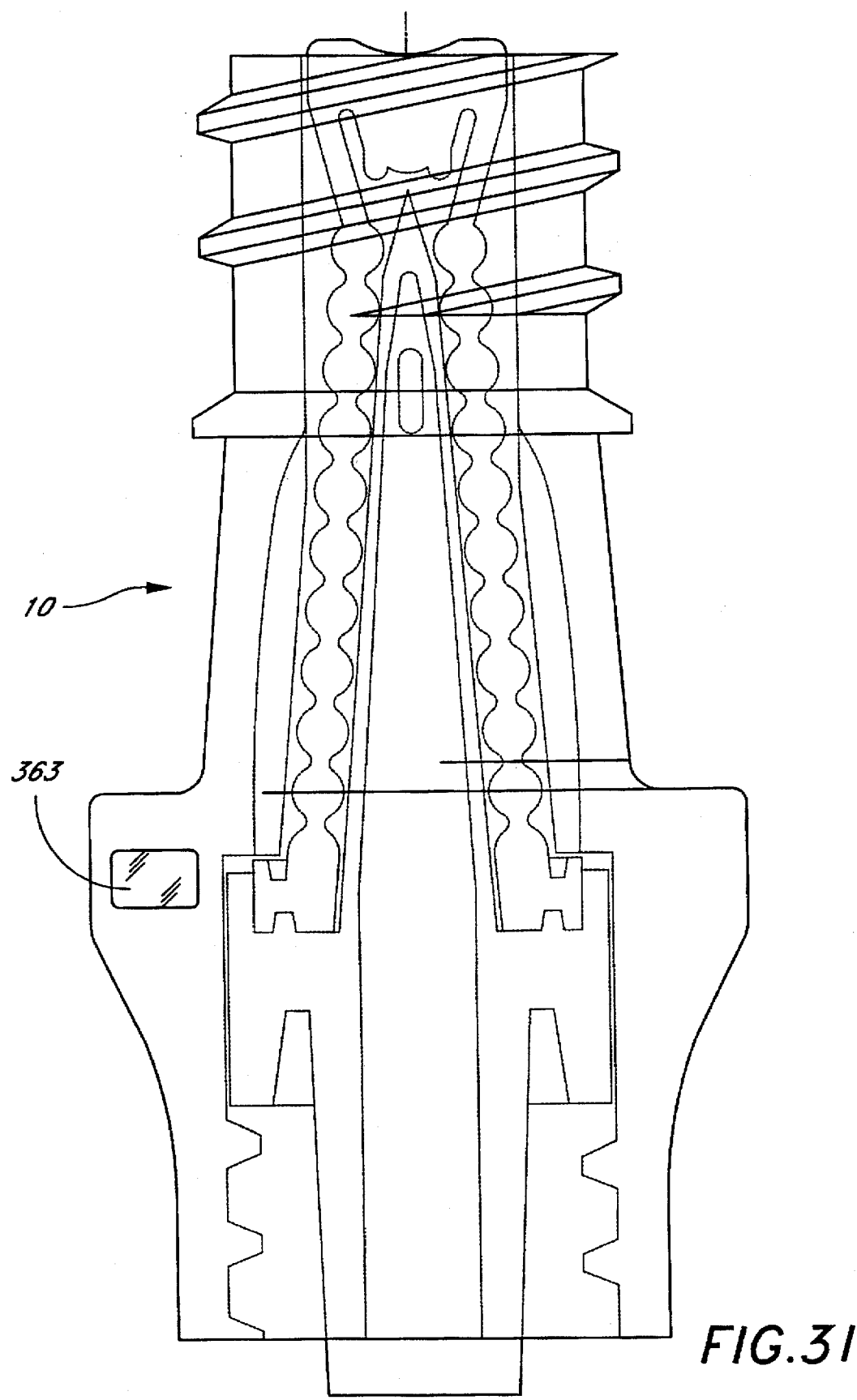
FIG. 31 is another alternative embodiment of the medical implement indicator of the present invention used in connection with the valve of FIG. 23.

Referring to FIG. 31, the medical implement indicator of the present invention may also take the form of an LED display 363 powered by a small battery (not shown) attached to a medical implement such as the valve 10. It is also contemplated by the present invention that a small battery-powered light bulb may be utilized in the same fashion as the LED display 363 to illuminate the valve 10 in a dark environment. As will be clearly recognized by those of skill in the art, an LED display or light bulb may be used with any medical implement in accordance with the teachings of the present invention.

MEDICAL IMPLEMENT INDICATOR IN USE

The medical implement indicator is particularly useful when a healthcare worker is required to administer medication to a patient in a dark environment. The healthcare worker simply enters the room of the patient in the dark and looks for the medical implement indicator that is emitting light in the darkened room. The healthcare worker locates the medical implement indicator in the dark in order to locate the medical implement to which it is affixed. The healthcare worker administers the medication to the patient by employing the medical implement that is illuminated by the medical implement indicator. The healthcare worker then exits the darkened room of the patient.

Moreover, should a healthcare worker set about to administer a medication to a patient in the dark whereby more than one medical implement needs to be manipulated, the healthcare worker merely proceeds as described above while introducing some simple modifications to the procedure. Upon entering the darkened room, the healthcare worker may identify many medical implement indicators therein. The glow cast by the indicators is sufficient to direct the worker to the medical implements indicated thereby. The healthcare worker is consequently in a position to distinguish which of the medical implements indicated are suitable for administering the medication to be given to the patient. In one such case, one of the medical implements appropriate to the task may constitute a medical valve. Another of the medical implements may include a delivery end through which may be transferred the medication from a source for delivery to the patient. The medical valve, in this case, is designed to have an opening configured and arranged to receive the delivery end of the medical implement through which the medication is to be dispatched. The healthcare worker is guided by the luminescence of, for example, glow rings attached to the medical valve and medical implement having a delivery end. After recognizing the appropriate medical implements by the light of, e.g., the annular rings, the worker inserts the delivery end of the medical implement into the medical valve. The illumination cast by the indicators is effective to facilitate the operation, thus precluding having to turn on the lights. The healthcare worker, in this manner, administers the medication from the source through the valve to the patient in the dark. Thereafter, the delivery end is withdrawn from the valve. The healthcare work subsequently exists the darkened room, leaving the patient to sleep uninterrupted by the perturbation of having the lights turned on.

SCOPE OF THE INVENTION

The above presents a description of several embodiments of the present invention, including the best mode contemplated of carrying out the present invention. The foregoing also provides the manner and process of making and using the invention, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention, as generally expressed by the following claims. These claims particularly point out and distinctly claim the subject matter of the invention.

What is claimed:

1. A medical flow apparatus that provides an indication of it location in a dark environment comprising:

a medical implement that facilitates the passage of fluids either to or from a patient, said implement having an outer housing having a first end and a second end, said ends adapted for mating engagement with another medical implement and said housing defining a fluid passage therethrough; and a visible light emitting device affixed to said medical implement, said device comprising an annular ring encircling a portion of said housing of said implement.

2. The apparatus in accordance with claim 1, wherein said light emitting device is positioned between said first and second ends of said implement.

3. The apparatus in accordance with claim 1, wherein said implement includes first and second outwardly extending flanges positioned on said housing and wherein said light emitting device is positioned between said flanges.

4. The apparatus in accordance with claim 1, wherein said light emitting device comprises a light emitting material.

5. The apparatus in accordance with claim 1, wherein said ring is tapered.

6. The apparatus in accordance with claim 1, wherein said ring has an inner surface and an outer surface, and wherein said inner surface has at least one ridge positioned on said internal surface for use in affixing said ring to said apparatus.

* * * * *

UNITED STATES PATENT AND TRADEMARK OFFICE
CERTIFICATE OF CORRECTION

PATENT NO. : 5,690,612
DATED : November 25, 1997
INVENTOR(S) : George A. Lopez, et. al.

It is certified that error appears in the above-identified patent and that said Letters Patent is hereby corrected as shown below:

```
Col. 3, line 8, should read --valve also includes--
Col. 7, line 9, should read --external portion of--
```

Signed and Sealed this

Thirtieth Day of June, 1998

*Attest:*

BRUCE LEHMAN

*Attesting Officer*          *Commissioner of Patents and Trademarks*